US011260206B2

(12) United States Patent
Stone et al.

(10) Patent No.: US 11,260,206 B2
(45) Date of Patent: Mar. 1, 2022

(54) INSERTION DEVICE FOR ONE-HANDED INSERTION OF A GUIDEWIRE INTO THE LUMEN OF A VESSEL/CAVITY

(71) Applicant: EVA Innovations, Inc., Aventura, FL (US)

(72) Inventors: Daniel B. Stone, Aventura, FL (US); Jeffrey A. Panozzo, Naples, FL (US)

(73) Assignee: EVA INNOVATIONS, INC., Avontura, FL (US)

( * ) Notice: Subject to any disclaimer, the term of this patent is extended or adjusted under 35 U.S.C. 154(b) by 363 days.

(21) Appl. No.: 16/345,797

(22) PCT Filed: Nov. 10, 2017

(86) PCT No.: PCT/US2017/061046
§ 371 (c)(1),
(2) Date: Apr. 29, 2019

(87) PCT Pub. No.: WO2018/089758
PCT Pub. Date: May 17, 2018

(65) Prior Publication Data
US 2019/0282788 A1 Sep. 19, 2019

Related U.S. Application Data

(60) Provisional application No. 62/420,269, filed on Nov. 10, 2016.

(51) Int. Cl.
A61M 25/09 (2006.01)
A61M 25/06 (2006.01)
(Continued)

(52) U.S. Cl.
CPC .... A61M 25/09041 (2013.01); A61M 25/065 (2013.01); A61M 39/10 (2013.01); A61B 2017/3405 (2013.01); A61M 25/0693 (2013.01)

(58) Field of Classification Search
None
See application file for complete search history.

(56) References Cited

U.S. PATENT DOCUMENTS 6,626,869 B1 * 9/2003 Bint ................ A61M 25/09041
604/158
2003/0229311 A1 * 12/2003 G. Morris ........... A61M 5/1456
604/151

(Continued)

FOREIGN PATENT DOCUMENTS

WO 1999012600 A1 3/1999
WO 2014118172 A1 8/2014

OTHER PUBLICATIONS

Extended European Search Report dated Jun. 30, 2020.

Primary Examiner — Bhisma Mehta
Assistant Examiner — Robert F Allen
(74) Attorney, Agent, or Firm — Robert Alexander; Michael Farrell; Anna Kinney

(57) ABSTRACT

A device for one-handed insertion of a guidewire into a vessel or cavity is provided. The device has a body, an actuator carriage, a guidewire feed, and a syringe. The body has a handle, a guideway, and a clip to retain the syringe. The syringe has a barrel and a plunger with a flange and a guidewire passage. The actuator carriage has a trigger and a clip to grasp the syringe plunger flange. The actuator carriage slides along the body guideway. The guidewire feed has a wire feed surface. The thumb engages wire at the wire feed surface to advance and retract the wire through the guidewire passage and a finger moves the trigger to move the syringe plunger rearwardly and/or forwardly, while the remaining fingers of the one hand grasp the handle. The device allows the user to sense resistance encountered by the tip of the wire.

15 Claims, 44 Drawing Sheets

(51) Int. Cl.
  *A61M 39/10*    (2006.01)
  *A61B 17/34*    (2006.01)

(56) References Cited

U.S. PATENT DOCUMENTS

| | | | | |
|---|---|---|---|---|
| 2015/0314104 | A1* | 11/2015 | Almansouri | A61M 25/0606 128/845 |
| 2016/0101267 | A1* | 4/2016 | Kelly | A61M 25/09 604/510 |
| 2016/0256621 | A1* | 9/2016 | Toro | A61M 5/008 |
| 2018/0296804 | A1* | 10/2018 | Bierman | A61M 39/06 |

* cited by examiner

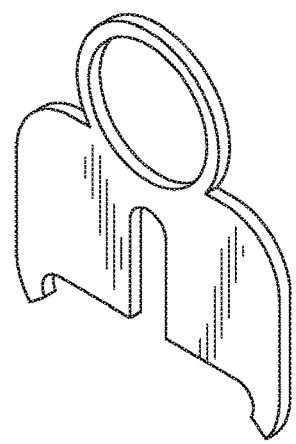
FIG. 4
FIG. 5
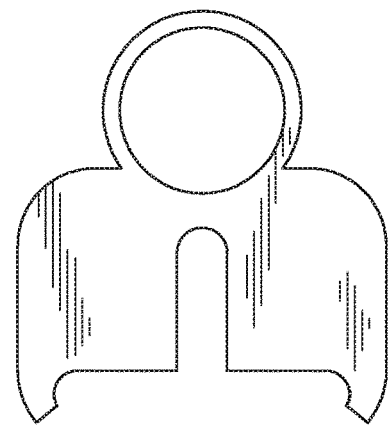
FIG. 6
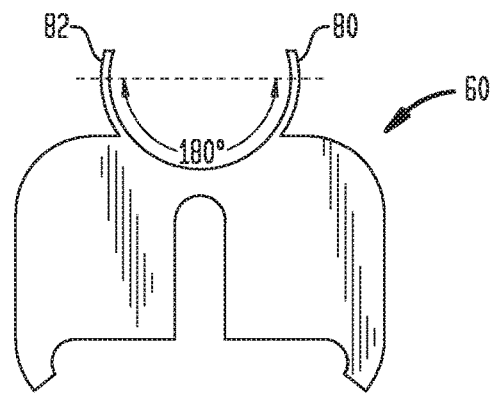
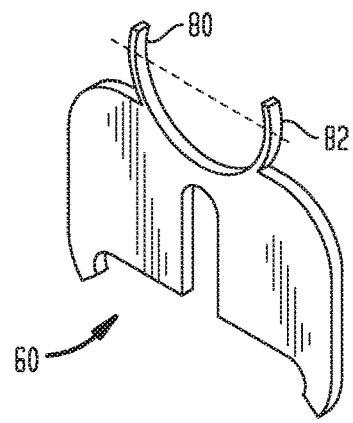
FIG. 7

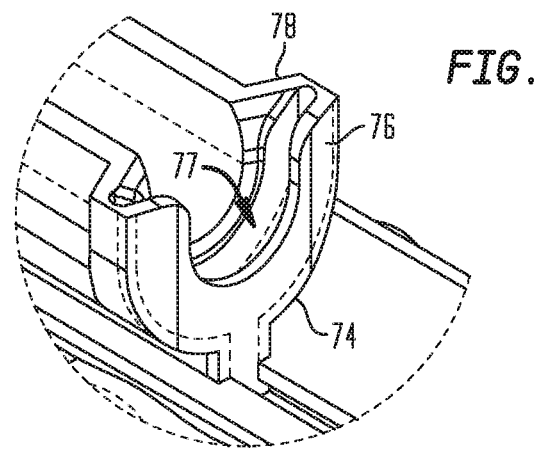
FIG. 77
FIG. 78
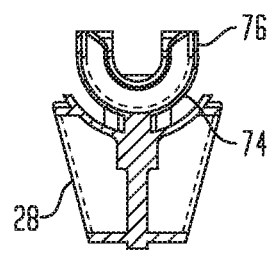
FIG. 79
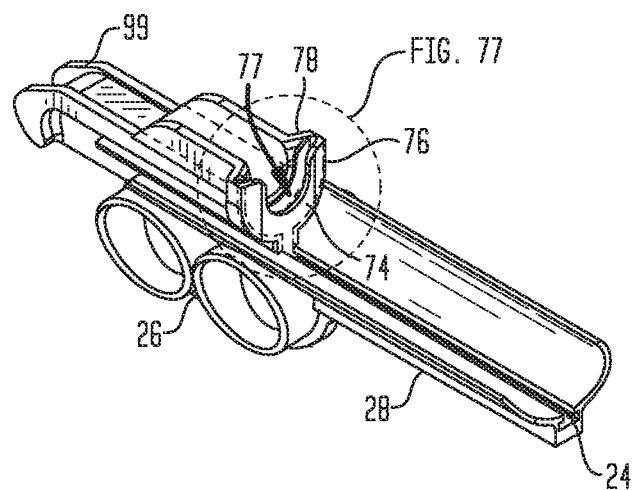

INSERTION DEVICE FOR ONE-HANDED INSERTION OF A GUIDEWIRE INTO THE LUMEN OF A VESSEL/CAVITY

CLAIM FOR PRIORITY

This application is a National Phase Entry of International Application PCT/US2017/61046, filed Nov. 10, 2017. PCT/US2017/61046 is based on U.S. Provisional Patent Application Ser. No. 62/420,269, filed on Nov. 10, 2016. The priority of the foregoing applications is hereby claimed, and their disclosures incorporated by reference.

BACKGROUND OF THE INVENTION

Insertion of a guidewire, particularly a central line of considerable length, into the lumen of a vessel can be a particularly technically difficult and time consuming procedure as it must often be accomplished quite rapidly when the patient is in distress; yet the common practical procedures heretofore available have largely either required the use of an assistant with an imaging device, typically an ultrasound, and concomitant coordination therewith, or have deprived the physician inserting the guidewire of the critical sense of feel and touch for the progress of the guidewire which can make a vital difference between successful and proper insertion of the guidewire into the vessel/cavity, penetrating only one wall thereof and failure occasioned by penetration of the opposite wall of the vessel/cavity or missing a critical turn in directing the wire to its desired location. Either situation can lead to an adverse outcome particularly in the case of a gunshot wound, rapid blood loss or any other situation making it critical to insert a wire into a vessel or cavity quickly and accurately. This invention relates to a device enabling the practitioner to introduce the guidewire into a vessel/cavity and advance it along the desired path using one hand, freeing the other to control other equipment such as an ultrasound, while retaining the critical sense of feel and touch to know both when the wire is advancing properly into the vessel/cavity and when the wire is attempting to deviate from the desired course. The ability to perceive the precise amount of resistance that the tip is experiencing, while leaving the other hand free for other devices, can be absolutely crucial to proper introduction of a guidewire and can literally make a difference between life and death. The procedure is applicable to central line placement in arteries and other circulatory vessels as well as for less common procedures in which it is desired to introduce a guidewire of considerable length into other organs in a living body for a variety of therapeutic reasons. It is particularly useful in retrograde intubation as time is almost always critical when retrograde intubation is called for.

SUMMARY OF THE INVENTION

There have been many attempts to address these issues previously. There are numerous patents directed to guidewires coiled in cassettes with a fixture at the exit to allow the practitioner to advance the guidewire into the vessel/cavity. However, these attempts cannot be considered entirely successful. In particular, where prior art devices have been claimed to make one-handed insertion and guidance possible, these often introduced gearing, drive wheels, or other devices between the operator's hand and the wire being introduced thereby degrading the operator's sense of feel for the precise amount of resistance being encountered by the guidewire. In this invention the guidewire is advanced by contact with the clinician's thumb enabling the clinician to gauge the amount of resistance being encountered while using the remainder of the hand to control advancement of the needle and manipulate the plunger of the syringe as required and leaving the other hand free to manipulate an ultrasound probe or transducer.

This invention addresses this issue by providing a device for one-handed insertion of a guidewire into the lumen of a vessel or other cavity, comprising: a body having: a rearwardly relieved handle, a guideway defined by said body, a clip mounted on said body adapted to receive and retain the barrel of a syringe; a syringe having: a barrel and a finger flange, said syringe being retained by said clip, a plunger having a plunger flange and a guidewire passage therethrough and a hollow needle co-linear with said guidewire passage through said plunger as illustrated schematically with a pair of parallel lines N on FIGS. 1, 29 and 58; an actuator carriage slidable along said guideway of said body, having attached thereto: a trigger, a flange trap adapted to grasp the plunger flange of said plunger of said syringe, a generally annular cassette mounted on said plunger of said syringe and having mounted therebetween a wire feed module having a receiver adapted to couple with said generally annular cassette, a rear wire control tube, a forward wire control tube, a wire feed surface between said rear wire control tube and said forward wire control tube, wherein said handle, said trigger and said feed surface are disposed such that when the handle is grasped by the digits of one hand, a digit of said one hand can urge the trigger and the plunger of said syringe rearwardly to create a slight pressure differential allowing fluid, whether liquid or gas, to flow through said needle into said syringe when said needle is properly positioned, a phenomenon often referred to as "flashback", or to withdraw fluid through said needle, if need be, while the digit of said one hand can advance and retract the wire through said syringe by engaging the wire between the digit and the feed surface, sensing resistance encountered by the tip of said wire. I term the embodiments of this invention having a downwardly extending handle as "pistol grip" fixtures. In many cases, pistol grip fixtures will have downwardly facing wire feed surfaces where the tip of the thumb engages the wire with the clinician's hand in a "thumbs-up" posture.

In many cases, the device of the present invention will be provided as a stand-alone device to be used with standardized guidewire cassettes having attached thereto: a forward wire module adapted to couple with said finger flange and direct said guidewire into said guidewire passage through the plunger of said syringe; and a wire feed surface between said generally annular cassette and said forward guide fitting, and a line insertion syringe having a barrel, a plunger having a plunger flange and a guidewire passage therethrough and a hollow needle co-linear with said guidewire passage through said plunger. In such a case, the present invention will comprise: a device for insertion of a guidewire disposed within a generally annular cassette through a syringe into the lumen of a vessel/cavity, comprising: a body having: a rearwardly relieved handle, a guideway defined by said body, a clip mounted on said body adapted to receive and retain the barrel of a syringe; an actuator carriage slidable along said guideway of said body, having attached thereto: a trigger, a flange trap adapted to grasp the plunger flange of said plunger of said syringe, a receiver adapted to couple with said generally annular cassette, wherein said handle, said trigger and said feed surface are disposed such that when the handle is grasped by the digits of one hand, a digit of said one hand can urge the trigger of said syringe rearwardly either to create a slight pressure differential allowing fluid to flow through said needle into said syringe when said needle is properly positioned, a phenomenon often referred to as "flashback", or to withdraw fluid through said needle, if need be, while the thumb of said one hand can advance and retract the wire through said syringe by engaging the wire between the thumb of said one hand and the wire feed surface, sensing resistance encountered by the tip of said wire.

An alternative embodiment of this invention addresses this issue by providing a device for one-handed insertion of a guidewire into the lumen of a vessel/cavity, comprising: a body having: a grip defined thereupon, a guideway defined by said body, a clip mounted on said body adapted to receive and retain the barrel of a syringe; a syringe having: a barrel and a finger flange, said syringe being retained by said clip, a plunger having a plunger flange and a guidewire passage therethrough and a hollow needle co-linear with said guidewire passage through said plunger; an actuator carriage slidable along said guideway of said body, having attached thereto: a trigger, a flange trap adapted to grasp the plunger flange of said plunger of said syringe, a generally annular cassette mounted on said plunger of said syringe and having mounted therebetween a wire feed module having a receiver adapted to couple with said generally annular cassette, a rear wire control tube, a forward wire control tube, a wire feed surface between said rear wire control tube and said forward wire control tube, wherein said grip, said trigger and said feed surface are disposed such that when the grip is grasped by the digits of one hand, a digit of said one hand can urge the trigger and the plunger of said syringe rearwardly to create a slight pressure differential allowing fluid to flow through said needle into said syringe when said needle is properly positioned, a phenomenon often referred to as "flashback", or to withdraw fluid through said needle, if need be, while the digit of said one hand can advance and retract the wire through said syringe by engaging the wire between the digit and the feed surface, sensing resistance encountered by the tip of said wire. I term the embodiments of this invention having a grip defined about the body as "hilt-handle" fixtures. In many cases, clinicians will find the hilt-handle fixtures preferable because it is easy to configure these devices such that the feed surface for the wire can be oriented facing upwardly so that the flat of the ball of the digit can be used to advance the wire giving the clinician excellent tactile feedback to the resistance that the wire is encountering while being advanced along the lumen of the vessel.

Preferred cassettes are substantially similar to those illustrated in Fleck, U.S. Pat. No. 5,125,906, Hand-Held Device for Feeding a Spring Wire Guide, issued Jun. 30, 1992, incorporated by reference herein in its entirety.

It is of particular importance that the operator is able to manipulate the wire with the digit, usually the thumb, of the hand holding the device as well as to manipulate the plunger with a digit of the same hand. The ability to manipulate the plunger using a digit of the same hand on the trigger enables the practitioner to urge the plunger of the syringe rearwardly creating a slight pressure differential enabling the practitioner to detect flashback, the ingress of blood or other fluid or matter into the syringe when the tip of the needle has entered the vessel or other structure. At the same time, the use of an ultrasound will enable the practitioner to ascertain when the tip of the needle has been properly placed. Being able to manipulate the fixture while gripping it enables the practitioner to have precise sensation of the amount of force required to advance the wire while leaving the other hand free to manipulate an imaging or sensing device, such as an ultrasound, so that the location of the needle can be visualized and thereafter the location of the tip of the guidewire can be visualized as it is advanced into the patient One-Handed Seldinger Technique As alluded to earlier, the raison d'être of the present invention is to allow clinicians to practice the Seldinger technique using only one hand for both needle placement as well as for manipulation of the guidewire while using the other to position a visualization device, such as an ultrasound, thus enabling the clinician to ensure that the ultrasound is placed properly for optimum viewing of the needle/guidewire as it enters the lumen while freeing assistants to perform other functions as needed. In many cases, where a central line is needed, time will absolutely be of the essence and the ability of the clinician to insert the line with minimal delay will be of the utmost importance. It is believed that reliable, expedient and practical methods of practicing the Seldinger technique while using only one hand to manipulate the syringe and guidewire and retaining a good haptic feel on the guidewire have not heretofore been available.

In the Seldinger technique, a syringe having a beveled needle is inserted into the body with the bevel oriented in such a fashion that the point of the bevel first enters the skin so that when the guidewire exits the bore of the syringe, it will be oriented generally parallel to the longitudinal axis of the body passageway in question or in some known other orientation if a guidewire is to be introduced into some other bodily structure. Where body conformation allows, it is usually preferable that the needle of the syringe make about a 45° angle with the surface of the skin with the point of the bevel engaging the skin first. As is well known, once the needle has entered the skin, the clinician applies slight negative pressure so as to be able to detect entry of the bore of the needle into the body passageway by flashback of blood, air, other body fluid, or even tissue into the barrel of the syringe. The fixtures of the present invention enable the clinician to apply this negative pressure by pulling back slightly on the plunger of the syringe with one hand whereas in the conventional technique the use of 2 hands can be somewhat awkward or clumsy. In many cases, the clinician will be able to manipulate the plunger using a single digit, perhaps the index finger, on the hand holding the fixture.

In those cases where an air embolism is possible, the use of the fixture of the present invention markedly decreases that danger as less effort is required to stabilize the needle, it will not be necessary to seal the pathway for air into the bore of the needle using the digit as in a conventional technique where the syringe is removed from needle. Further, as the guidewire will usually be joined to the syringe beforehand, there will be no need to either search out or insert in the guidewire as might otherwise be required in the clamor of an urgent procedure.

Once the guidewire is passing through the bore of the needle, the clinician may have increased ability to perceive the amount of resistance being encountered by the wire while also being able to more expeditiously use the ultrasound to ensure the guidewire enters into, and remains in, the lumen of the vessel or other desired location. This can be extremely significant as it avoids the contingencies in which the clinician might be tempted to withdraw the guidewire slightly to re-orient it in the lumen of the vessel. In particular, if such a withdrawal is not handled properly there is a possibility that the guidewire may be cut by the bevel on the needle particularly when the guidewire is curved at the tip or is for some other reason bent. In many cases, it is of course conventional, for the guidewire to have a "J" shaped tip to guard against inadvertent perforation of a vessel wall.

After the guidewire is properly positioned, in the conventional procedure, the clinician restrains the guidewire with one hand and retracts the needle with his other hand. In contrast, with the fixture of the present invention, the clinician moves the fixture rearwardly and only is required to begin using his other hand to restrain the guidewire as the bevel of the needle exits the body since the grip of surrounding tissue will often be sufficient to hold the guidewire in place while the fixture is being withdrawn, particularly if light restraint is applied above the entry point.

Once the guidewire has been properly positioned, and the means of inserting it have been cleared away, the clinician using the fixture of the present invention will proceed generally in accordance with the conventional procedure.

At present, Arrow®/Teleflex® offers a peripheral catheter styled "Endurance" extended dwell peripheral catheter adapted to be inserted with one hand. Arrow®/Teleflex® are registered trademarks of Teleflex, Inc. See web site at teleflex.com. It is submitted that the style of catheter insertion fixture is, as advertised, suitable for peripheral catheters but is not readily adaptable for insertion of central lines, or guidewires therefor, as the tube of the catheter is deployed around the needle during the insertion procedure while the guidewire therefor may be advanced through the needle by urging a guidewire slider rearwardly, the interposition of the slider possibly interfering with the clinician's tactile feedback during manipulation of the wire. Thus, it is noted that, apparently, the maximum length of catheter currently offered in this format is about 8 cm, while the guidewires used for central line placement often have lengths of a half meter or more. In the procedure of the present invention, once the guidewire has been inserted into the vessel or other bodily structure, the fixture is removed, and the central line passed over the guidewire into the vessel, thereby allowing use of a central line of an indefinite length. Particularly in the case where the central line is being inserted through the groin and must extend into the region of the heart or coronary arteries, it is quite common to use a guidewire having a length of substantially over one meter.

Other aspects and advantages of the present invention are described in the detailed description below and in the claims.

BRIEF DESCRIPTION OF THE DRAWINGS

The invention is described in detail below with reference to the appended drawings, wherein like numerals designate similar parts. In the Figures:

FIGS. 4 and 5 illustrate the details of the syringe retention ring at the front of the body;

FIGS. 6 and 7 illustrate the details of the syringe retention clip at the rear of the body;

FIG. 48 is a detail of finger flange slot 68 in FIG. 39, while FIG. 44 is a detail of FIG. 41 illustrating finger flange slot 68 with finger flange 66 in situ and FIG. 43 is a sectional view along line 43-43 of FIG. 45, FIG. 50 is a sectional view along line 50-50 of FIG. 54;

FIG. 76 is a detail of finger flange slot 68 in FIG. 67, while FIG. 71 is a detail of FIG. 68 illustrating finger flange slot 68 with finger flange 66 in situ and FIG. 70 is a sectional view along line 70-70 of FIG. 73;

FIGS. 77-83 are detail views illustrating mounting features for ensuring reliable, hold fast, snap-into-position placement of the flange on the plunger of the syringe;

DESCRIPTION OF PREFERRED EMBODIMENTS

Figure 1:
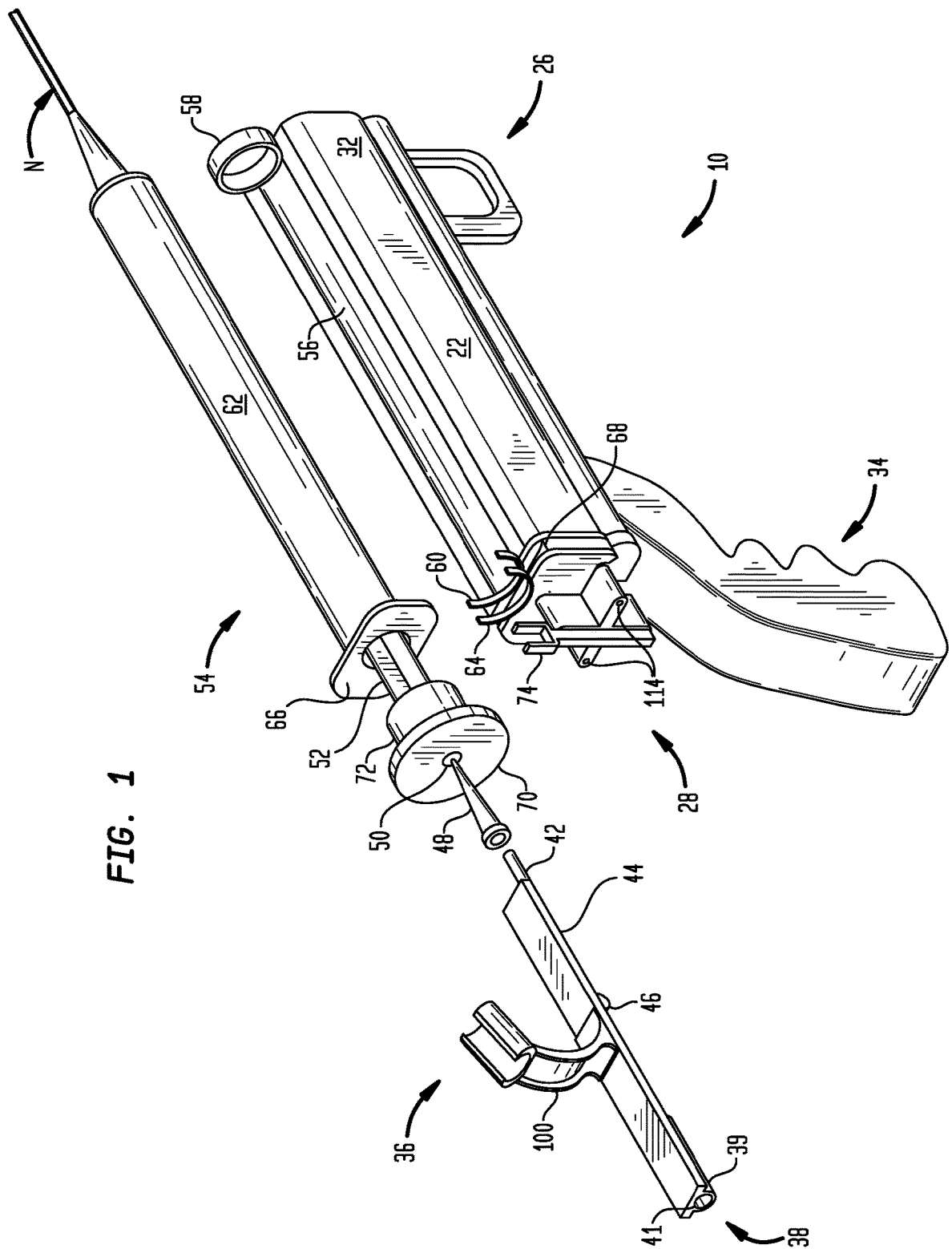
FIG. 1 is a schematic isometric perspective of an insertion device of the present invention, partially exploded, showing the plunger of the syringe in position prior to attachment of the guidewire feed module.
Figure 2:
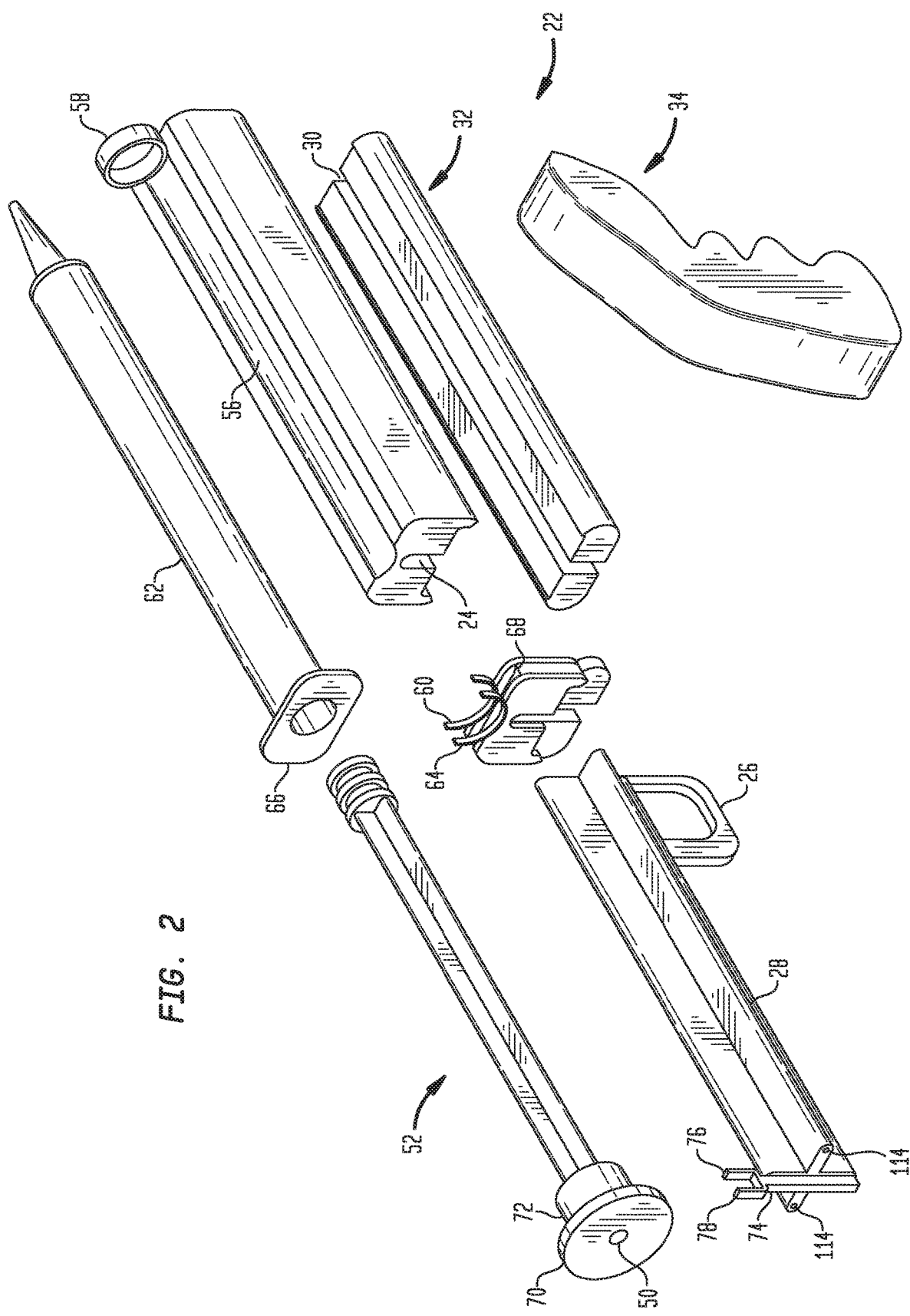
FIG. 2 is an exploded schematic isometric perspective of an insertion device of the present invention.
Figure 3:
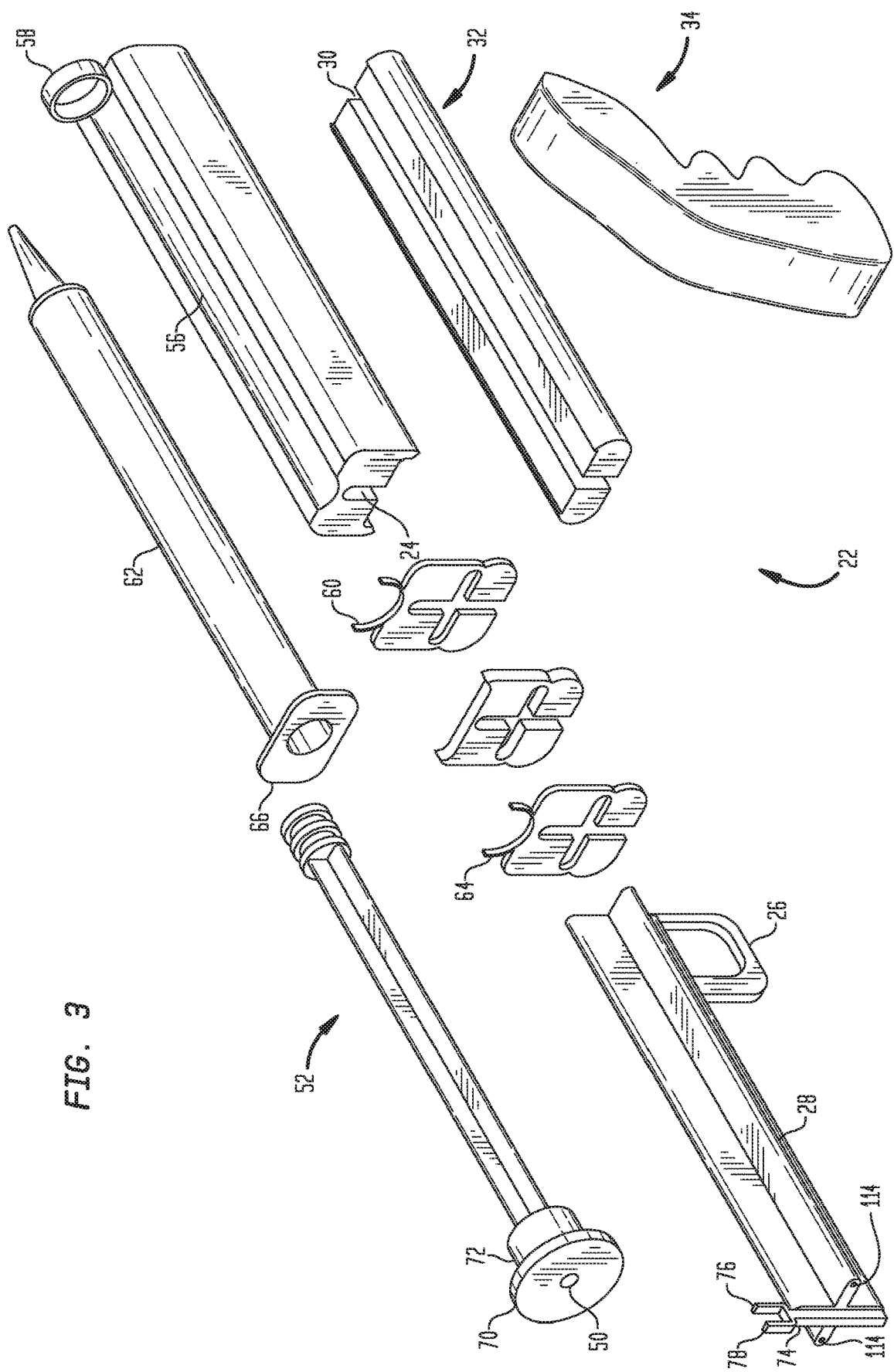
FIG. 3 is an exploded schematic isometric perspective of an insertion device of the present invention, showing details of the finger flange retention clip which retains the syringe upon the body while fixing the finger flange of the syringe in location longitudinally.

The invention is described in detail below with reference to several embodiments and numerous examples. Such discussion is for purposes of illustration only. Modifications to particular examples within the spirit and scope of the present invention, set forth in the appended claims, will be readily apparent to one of skill in the art. Terminology used herein is given its ordinary meaning consistent with the exemplary definitions set forth immediately below.

With respect to the various ranges set forth herein, any upper limit recited may, of course, be combined with any lower limit for selected sub-ranges.

The transitional phrase "consisting essentially of" limits the scope of a claim to the specified materials or steps "and those that do not materially affect the basic and novel characteristic(s)" of the claimed invention. As used herein with respect to article claims, "consisting essentially or and like terminology refers to the recited components and excludes other components which would substantially change the basic and novel characteristics of" the article. Unless otherwise indicated or readily apparent, an article consists essentially of the recited components when the article includes 90% or more by weight of the recited components. That is, the terminology excludes more than 10% unrecited components.

In FIGS. 1 through 8, insertion device 10 is adapted to allow one-handed insertion of guidewire 12. Guidewire 12 is commonly disposed within generally annular cassette 14 having exit opening 16. Insertion device 10 comprises body 22 with longitudinally extending guideway 24 defined therethrough. Actuator 28 sliding within longitudinally extending guideway 24 has trigger 26 mounted thereupon which trigger 26 slides within longitudinally extending slot 30 defined in lower forward portion 32 of body 22. Rearwardly extending handle 34 attached to body 22 is highly relieved.

Guidewire 12 may be withdrawn from generally annular cassette 14 through wire guide feed module 36 mounted thereupon at exit 16. Wire guide feed module 36 comprises: receiver 38 adapted to couple with exit 16 of generally annular cassette 14; rear wire guide 39 having rear tube 41 defined therethrough; forward guide fitting 40 comprising forward tube 42 with feed surface 44 being defined between rear tube 41 and forward tube 42. Preferably medial ridge or salient 46 is defined on feed surface 44 to ease and facilitate handling and control of guidewire 12. Forward guide fitting 40 is adapted to mate with adapter cone 48 which is capable of penetrating and being frictionally retained within guide wire passage 50 of plunger 52 of syringe 54 which is carried in groove 56 defined atop body 22 of insertion device 10. Syringe 54 is retained in position by forward ring 58 and barrel clip 60 grasping barrel 62 of syringe 54. Longitudinal movement of barrel 62 of syringe 54 is restrained by finger flange stop 64 located just rearwardly of barrel clip 60 such that finger flange 66 is trapped between finger flange stop 64 and barrel clip 60. Finger flange 66 rests within finger flange slot 68. Plunger flange 70 is joined to plunger 52 via plunger header 72. Plunger flange clip 74 mounted on actuator 28 grasps plunger flange 70 between arms 76 and 78 defining groove 77 so that plunger 52 may be advanced or withdrawn within barrel 62 by manipulation of trigger 26. As shown in FIGS. 6 and 7, resilient arms 80 and 82 of barrel clip 60 embrace more than 180° of the circumference of barrel 62 urging it downwardly into groove 56 atop body 22 of insertion device 10 while forward ring 58 further restrains both lateral and longitudinal motion of barrel 62.

Dimensions, configuration and orientation of the foregoing parts are chosen such that when actuator 28, sliding along guideway 24 in body 22, is somewhat retracted from body 22 of insertion device 10, feed surface 44 for guidewire 12, and particularly medial ridge 46, is conveniently reachable by the digit of the hand grasping handle 34 while another digit of that same hand controls trigger 26. (Throughout this specification and claims, where we refer to "digit" we are referring to the digits of the hand, particularly any of the fingers or the thumb.) Accordingly, guidewire 12 located within guidewire cassette 14 may be drawn through guidewire exit opening 16 as the tip of the digit on the hand grasping handle 34 urges guidewire 12 forwardly or rearwardly by forward or rearward movement across medial ridge and guidewire 12 may be thereby advanced into the vessel/cavity with the operator being able to accurately sense the degree or amount of resistance guidewire 12 encounters as it is being advanced.

Figure 8:
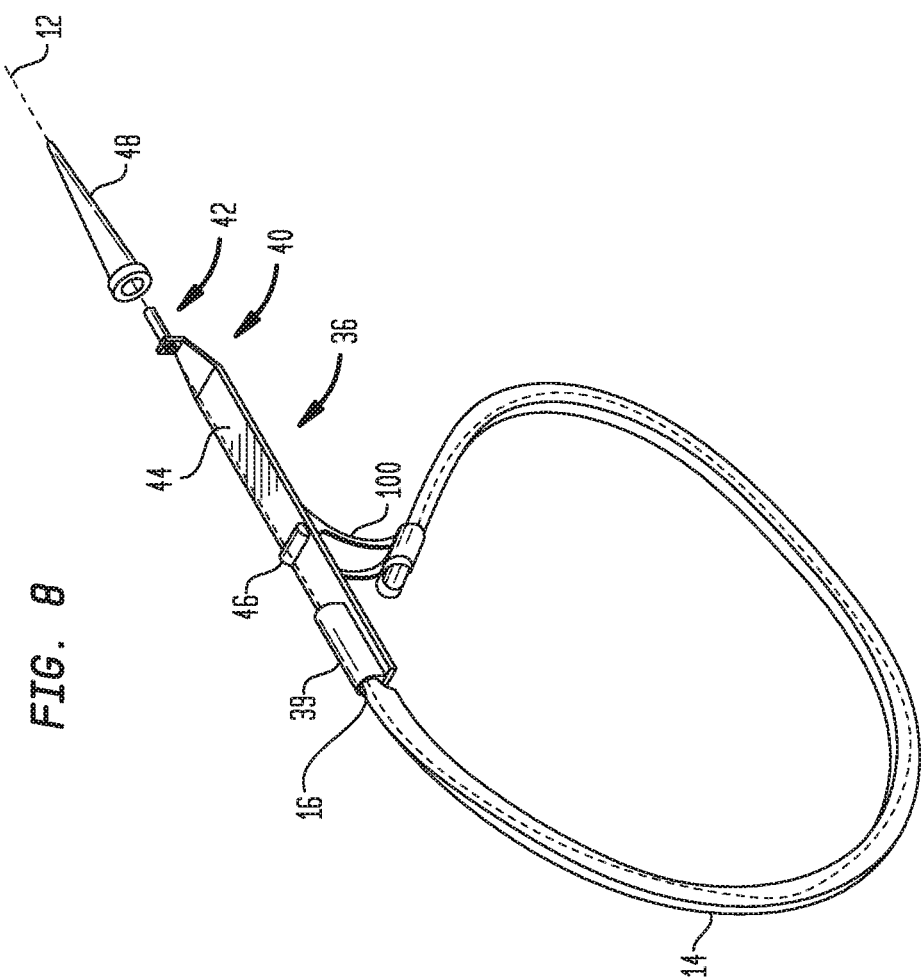
FIG. 8 is a schematic isometric perspective of a wire guide feed module suitable for use with an insertion device of the present invention.
Figure 9:
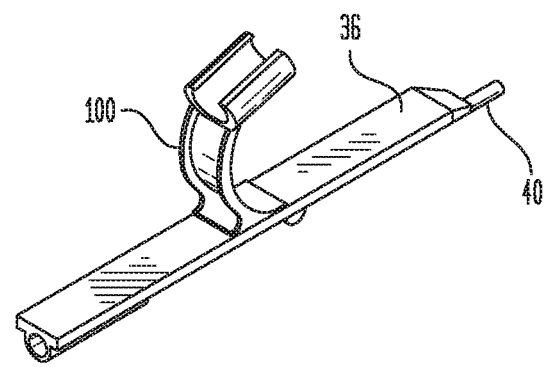
FIGS. 9-13 illustrate the details of the wire guide feed module of FIG. 8 particularly illustrating the medial salient preferred for enhanced haptics during wire manipulation.
Figure 10:
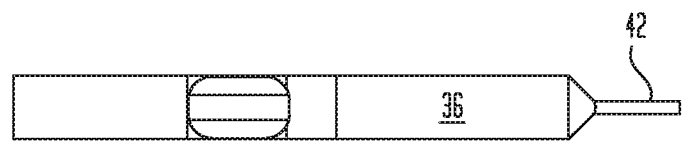
Figure 11:
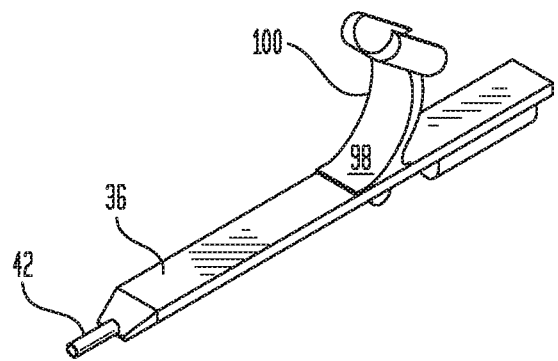
Figure 12:
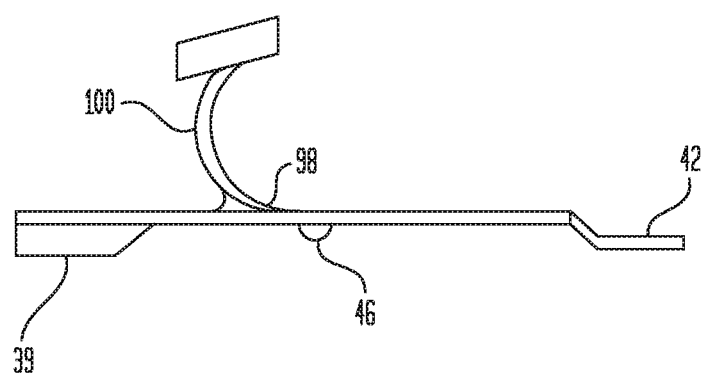
Figure 13:
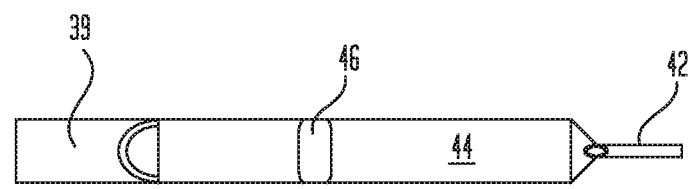
Figure 14:
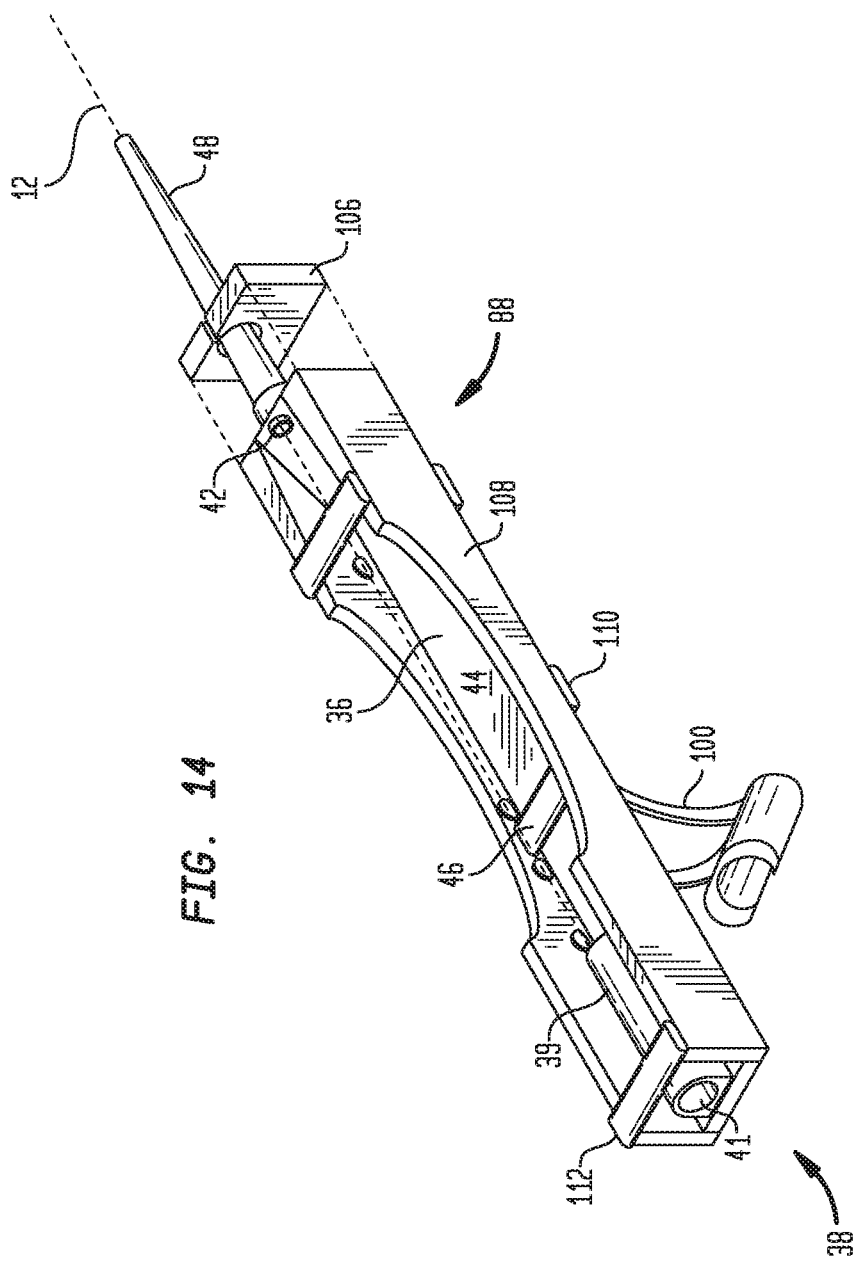
FIGS. 14 and 15 illustrate the lower surface of the wire guide feed of FIGS. 8-13 when mounted in a wire guide feed mounting fixture or retainer making it possible to mount the wire guide feed and a large cassette on the actuator carriage rather than the syringe when the cassette is of a size which is less conducive to mounting on the plunger of the syringe.
Figure 15:
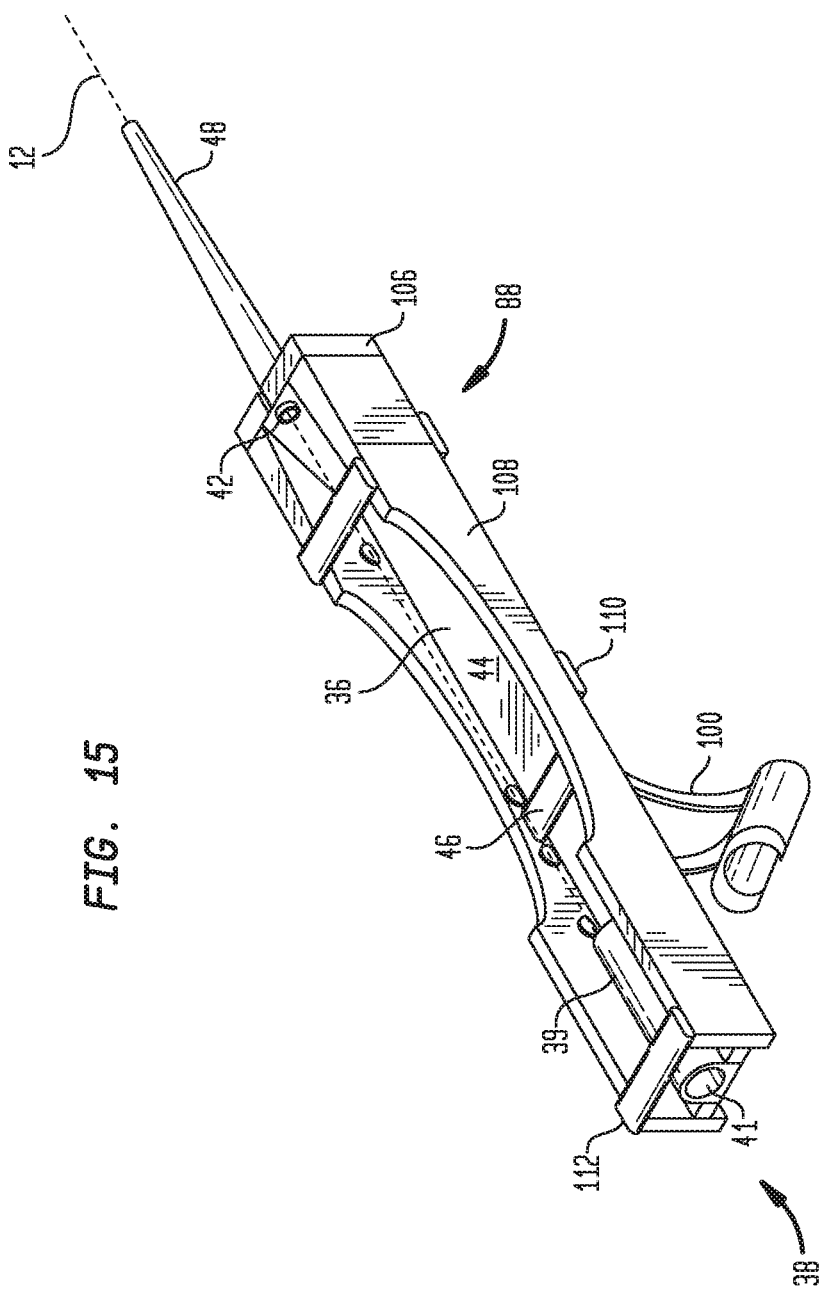

FIG. 8 is an illustration of a guidewire cassette 14 having guidewire 12 disposed therein with wire guide feed module 36 attached to exit 16 of guidewire cassette with wire 12 extending across feed surface 44 and medial ridge 46 through forward tube 42 in forward guide fitting 40 thence through adapter cone 48.

FIGS. 9 through 13 illustrate a hand-held device for feeding a spring wire guide substantially similar to that described in Fleck, U.S. Pat. No. 5,125,906 which we have described as wire guide feed module 36 herein.

In many cases, it will be possible to mount wire guide feed module 36 directly on plunger 52 by insertion of adapter cone 48 into guidewire passage 50 in plunger 52, particularly when the length of wire 12 required is relatively short and accordingly cassette 14 can be relatively light and thus be capable of being retained in position by frictional forces between forward guide fitting 40, adapter cone 48 and plunger 52. However, in some cases, a more robust mounting method is appropriate such as, for example when the weight of cassette 14 is too great or when pressure might be applied to wire guide feed module 36. For such occasions, we provide retainer 88 as illustrated in FIGS. 14 through 22 which is capable of being mounted on actuator 28. In such cases, however it is necessary to ensure that the operator has open, or as near to unrestricted as may be practicable, access to wires 12 as it passes over medial ridge 46 in feed surface 44 of wire guide feed module 36. Wire guide feed module 36 can be introduced into retainer 88 longitudinally, snapping into place when properly positioned thereby providing haptic feedback to the operator confirming completion of proper insertion.

Figure 16:
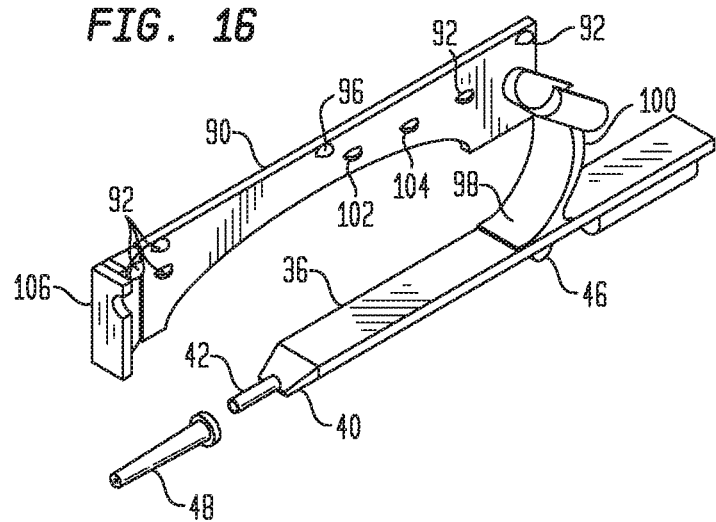
FIGS. 16-21 illustrate the details of the wire guide feed mounting fixture or retainer of FIGS. 14 and 15.
Figure 17:
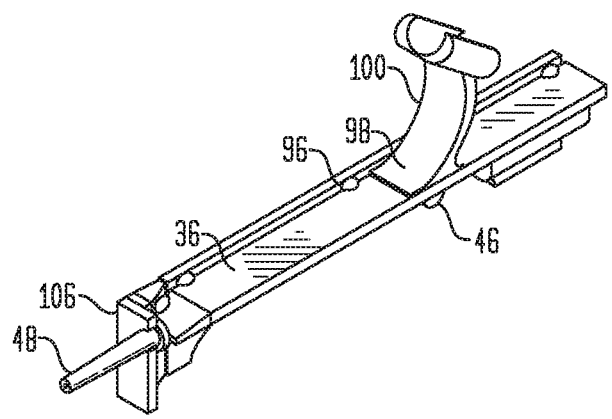
Figure 18:
Figure 19:
Figure 20:
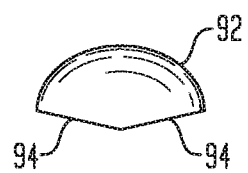
Figure 21:
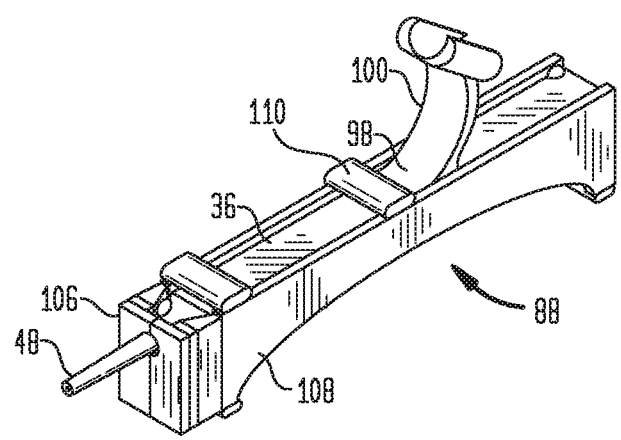
Figure 22:
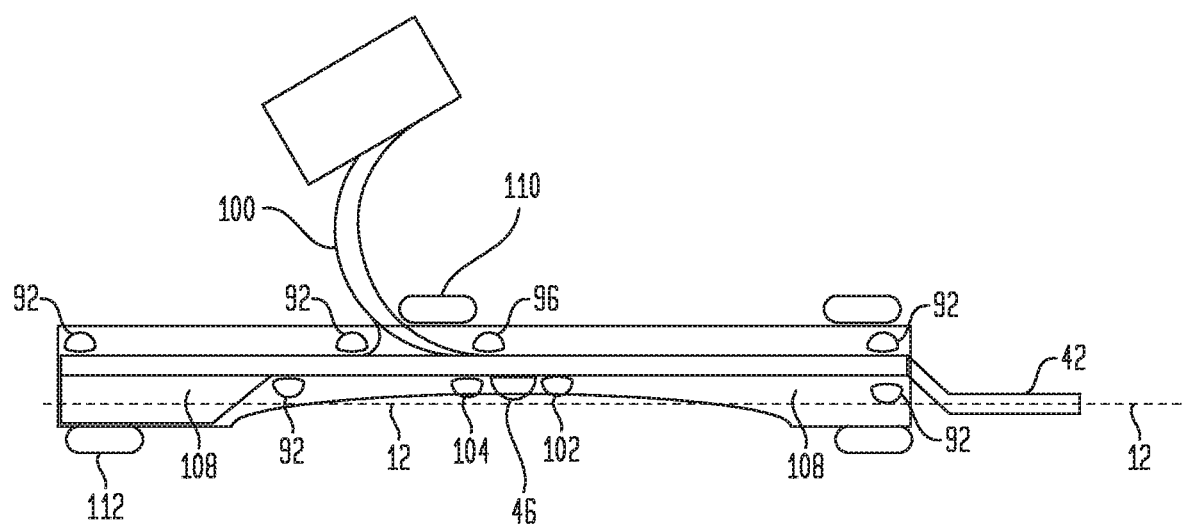
FIG. 22 is a schematic illustrating the details of the click to fit retention mechanism for holding the wire guide feed of FIGS. 8-13 in the wire guide feed mounting fixture or retainer of FIGS. 14-21.

As shown in FIG. 16, right sidewall 90 of retainer 88 has positioning protrusions 92 placed to locate wire guide feed module 36. FIGS. 19 and 20 illustrate the configuration of positioning protrusions 92 which generally have the shape of one fourth of a sphere with relieved flanks 94 as shown in FIG. 20 which help to guide wire guide feed module 36 into position. Notably protrusion 96 will bear against forward surface 98 of cassette mounting pylon 100, while protrusions 102 will bear against medial ridge 46 and protrusions 104 will snap into position as soon as medial ridge 46 has advanced into position. In the embodiment shown in FIGS. 14 through 22, adapter cone 48 is disposed within retainer 88. In alternative embodiments, it may be disposed forwardly of wall 106 of retainer 88. In FIG. 21, retainer 88 is shown with left side wall 108 in position with crossbar 110 preventing over insertion of wire guide feed module 36 into retainer 88 by interference with pylon 100. Notably, sidewalls 90 and 108 are highly scarfed away adjacent medial ridge 46 to allow the operator free access thereto. In FIG. 22, it can be appreciated how crossbar 112 prevents improper insertion of wire guide feed module 36, while crossbar 110 prevents over insertion and protrusions 102 and 104 signal complete insertion hapticly to the operator. It can also be appreciated that access to medial ridge 46 and guidewire 12 passing thereover is facilitated by scarfing the way of medial portion of sidewalls 90 and 108.

Figure 23:
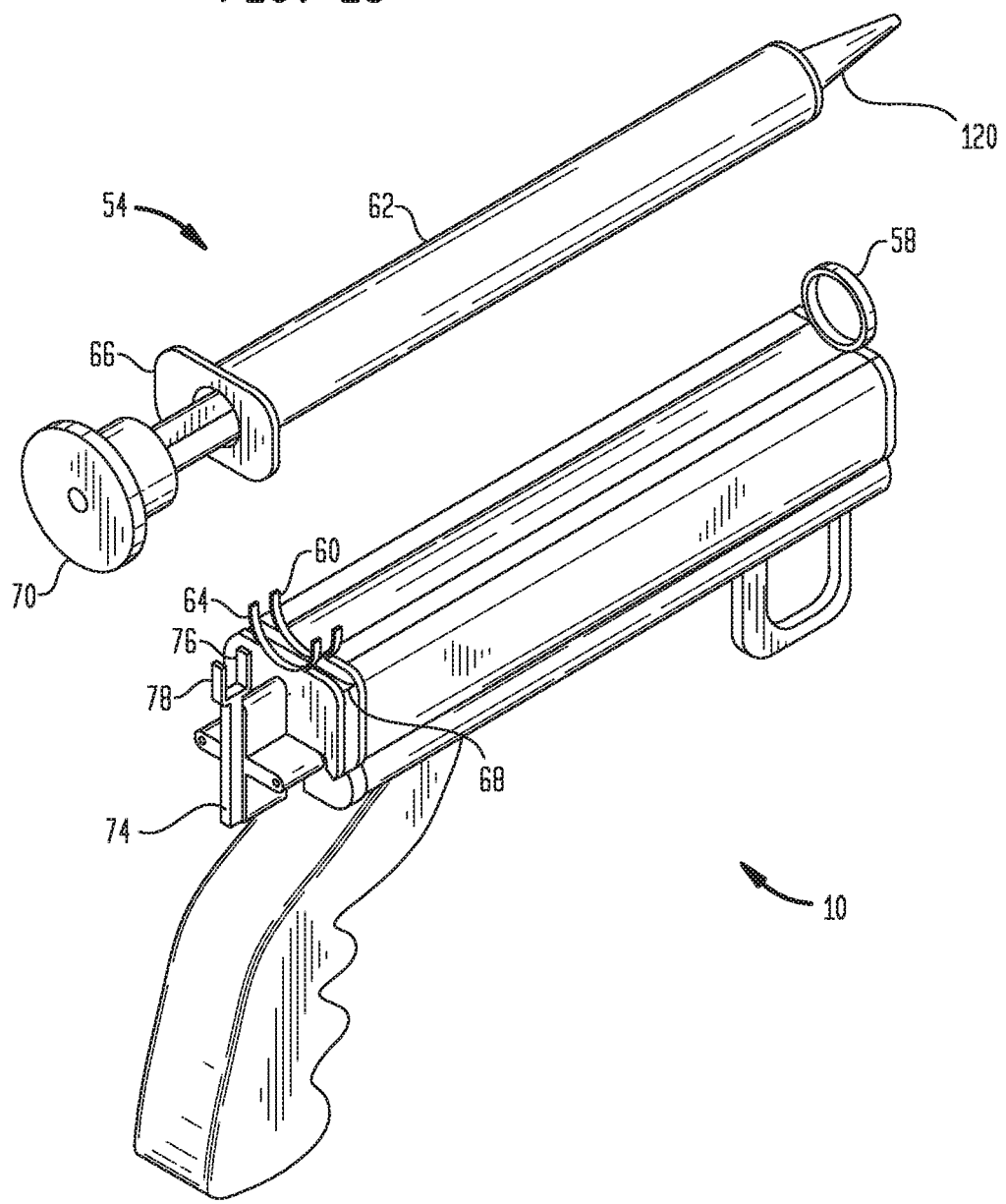
FIG. 23 is a schematic isometric perspective of an insertion device of the present invention with the syringe just above the mating clips on the body and actuating carriage.

FIG. 23 illustrates an assembled insertion device 10 with syringe 54 disposed thereabove. It can be appreciated how forward end 120 of syringe 54 will be restrained by forward retention ring 58 while finger flange 66 and barrel 62 will be restrained by finger flange stop 64, finger flange slot 68 and barrel clip 60 while plunger flange 70 is restrained by arms 76 and 78 of plunger flange clip 74.

Figure 24:
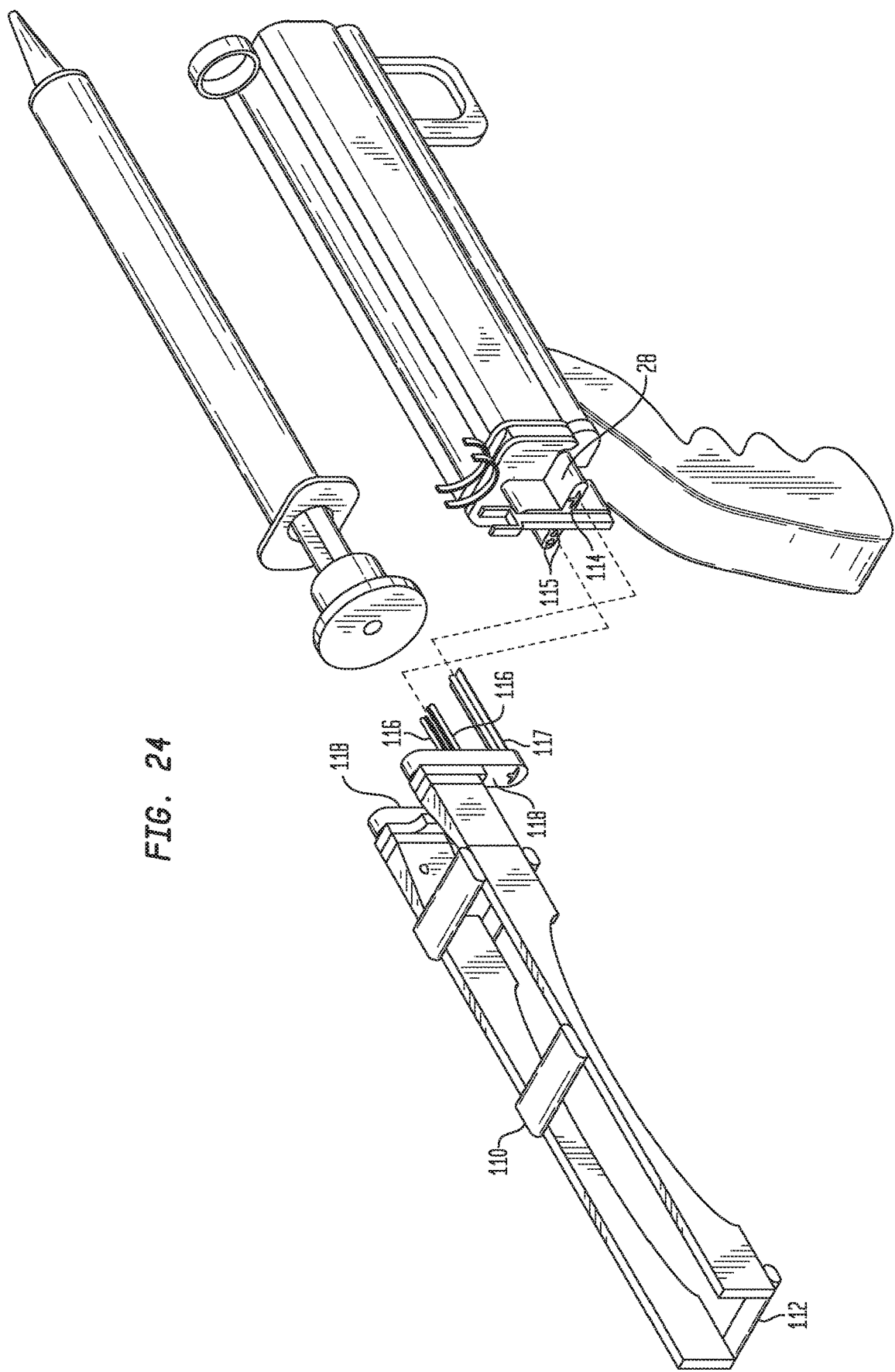
FIG. 24 is a schematic isometric perspective of a wire guide feed mounting fixture illustrating mounting thereof on the actuating carriage prior to insertion of the wire guide feed.
Figure 25:
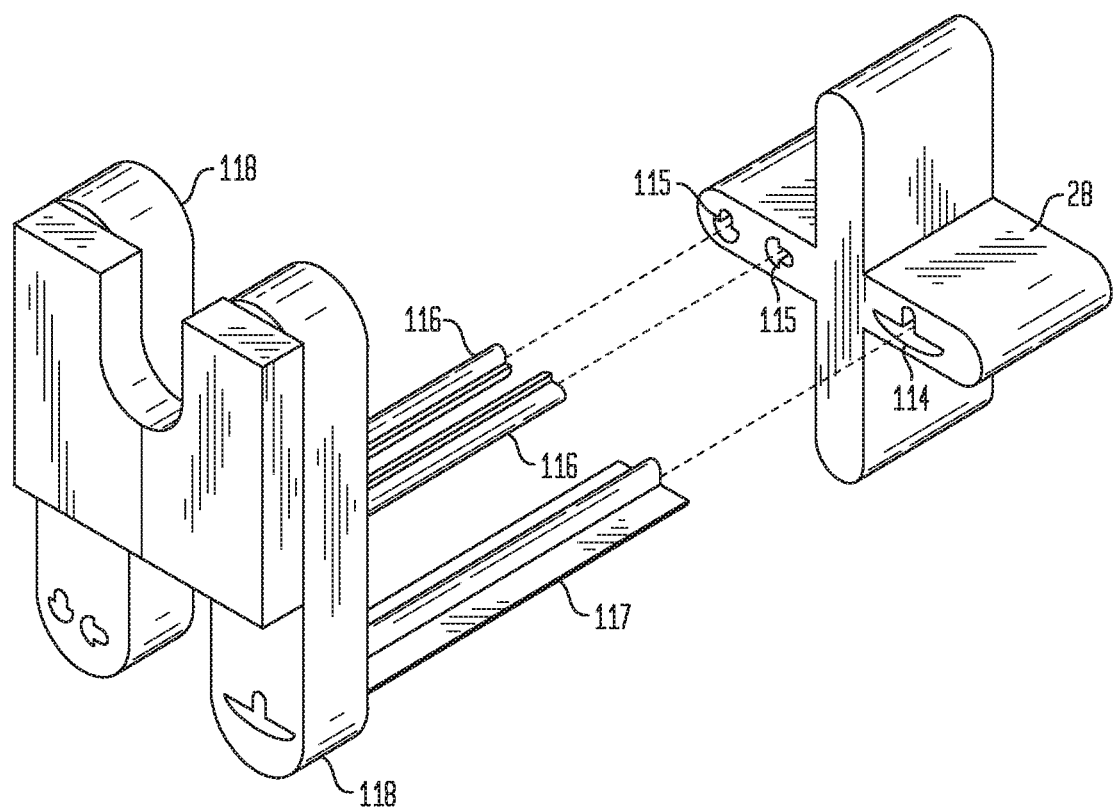
FIG. 25 is an enlarged schematic isometric perspective of the wire guide feed mounting fixture of FIG. 24 illustrating details of the mounting mechanism preventing incorrect mounting of the retainer on the actuating carriage prior to insertion of the wire guide feed module.

In FIGS. 24 and 25, mounting recesses 114 and 115 have been provided in actuator 28 whereby pin 116 and slat 117 on mounting arms 118 may be inserted to mount retainer 88 fast to actuator 28 with details being illustrated in FIG. 25. Inasmuch as slat 117 is too large, too wide, to be inserted into mounting recess 115, improper mounting of retainer 88 and guidewire cassette 14 is thereby prevented. Alternatively, insertion device 10 can be provided with retainer 88 permanently attached to actuator carriage 28.

Figure 26:
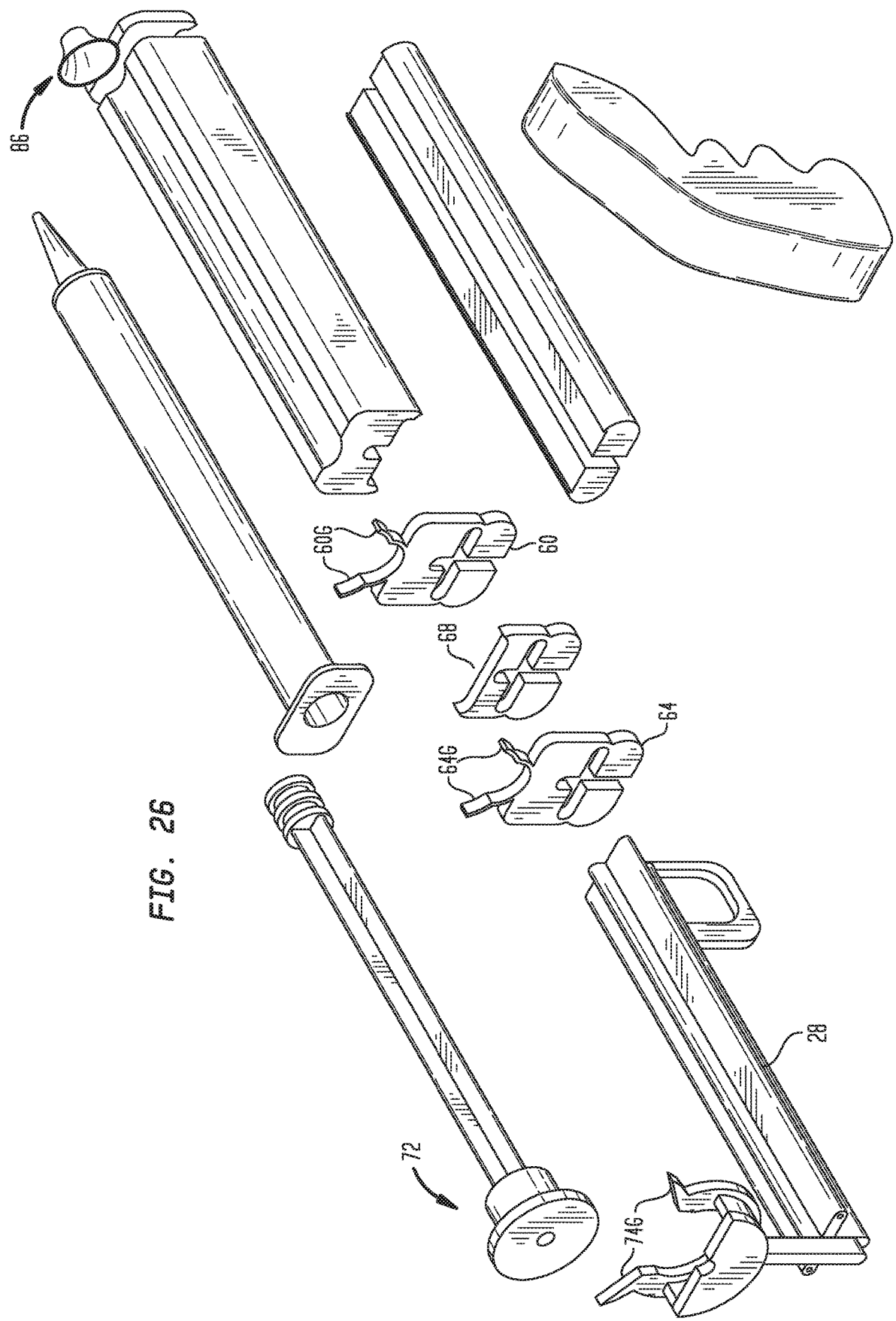
FIG. 26 is a schematic isometric perspective illustrating an alternative insertion device of the present invention which is configured to allow the operator to positively and quickly mount the syringe on the insertion device.
Figure 27:
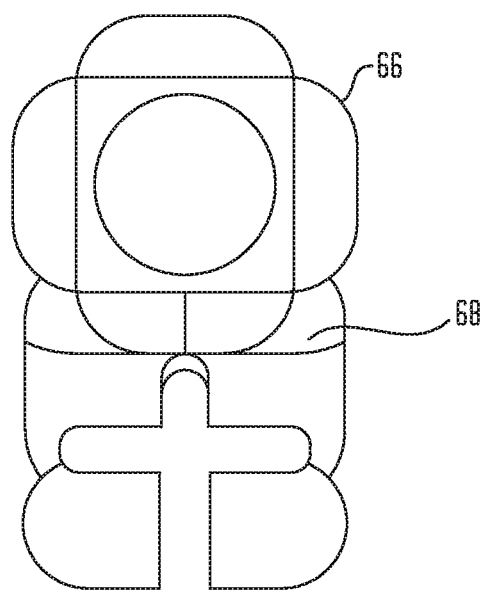
FIG. 27 is a detail drawing of the schematic isometric perspective of FIG. 26 illustrating the interaction of the finger flange on the syringe with its mating groove in the body.
Figure 28:
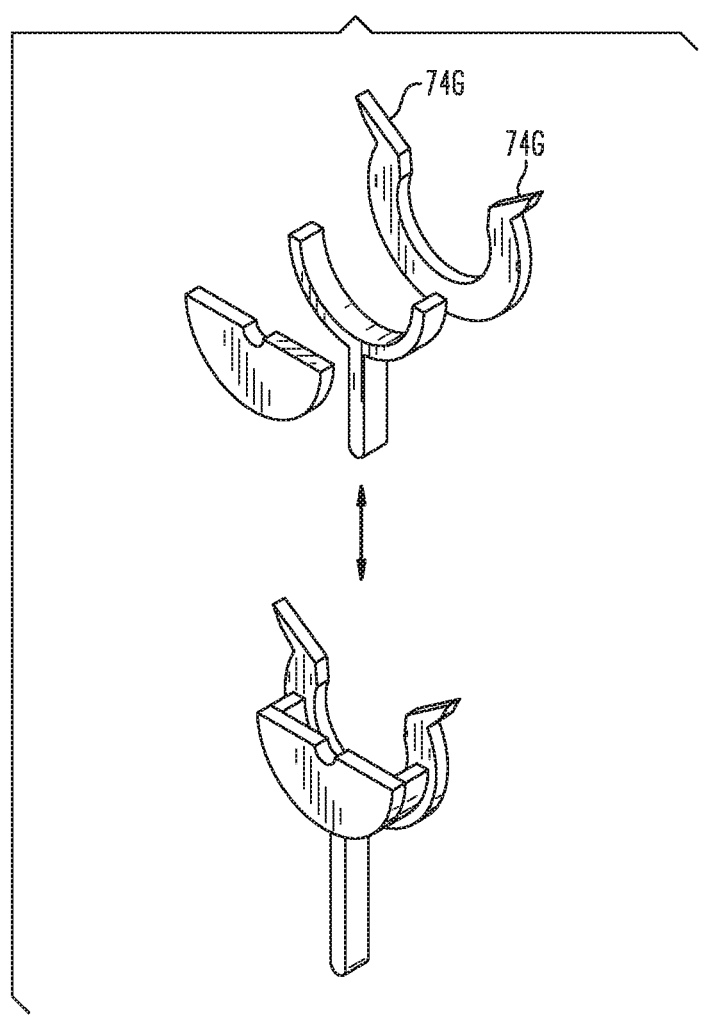
FIG. 28 is an exploded view illustrating details of the plunger flange clip of FIG. 26.
Figure 28A:
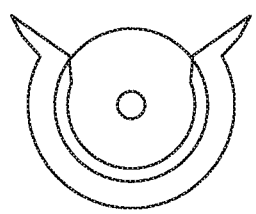
FIG. 28A is a detail drawing of the schematic isometric perspective of FIG. 26 illustrating the interaction of the plunger flange with the plunger flange clip.

FIGS. 26 through 28 illustrate a variant of the insertion device 10 of the present invention meant for situations such as emergency rooms in which the operator may be required to assemble the insertion device 10, syringe 54, wire guide feed module 36 and cassette 14 with considerable urgency. It can be appreciated that retention ring 58 has been replaced by retention cone 86, while finger flange stop 64, barrel clip 60 and plunger flange clip 74 have been provided with exterior guides 64G, 60G and 74G to facilitate rapid insertion of the mating portions of syringe 54 thereinto. FIG. 27 illustrates how finger flange 66 can be mounted either horizontally or vertically in finger flange slot 68. Similarly, FIG. 28 illustrates mating of plunger flange 70 with plunger flange clip 74.

FIGS. 29 through 38 illustrate a manufacturing design for a hilt grip fixture of the present invention wherein parts performing the same function are given the same numbers as those performing that function in the conceptual design of a pistol grip fixture illustrated in FIGS. 1 through 28. It will be apparent that the primary difference between the two designs is that the grip is incorporated into body 22 of the fixture of FIGS. 29-38 and adapter/receiver 36 for annular wire cassette 14 is oriented with feed surface 44 oriented upwardly so that a clinician holding the insertion device 10 such as a fixture 10 is able to manipulate guidewire 12 with the flat of his digit while using his index finger to advance and retract actuator 28 while engaging plunger flange 70 of syringe 54 providing an enhanced haptic feel to evaluate resistance being met by guidewire 12 as it is advanced into the body.

Figure 29:
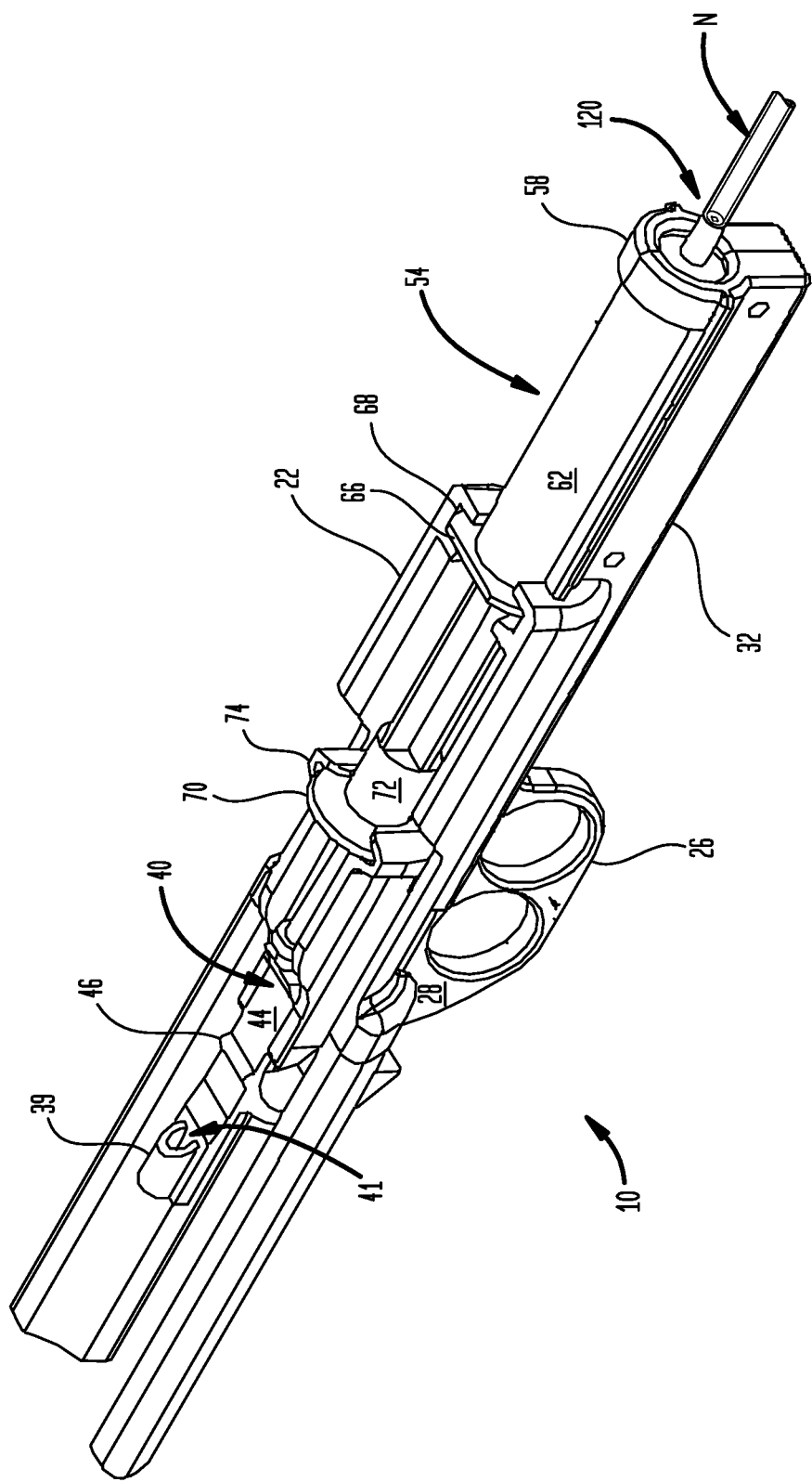
FIGS. 29 and 30 illustrate an alternative embodiment of the present invention which many clinicians may find preferable ergonomically as it positions the wire control surface above the trigger mechanism with the wire control surface facing upwardly so that the wire is more easily engaged by the flat of the digit rather than the tip of the digit as in the previous embodiment.
Figure 30:
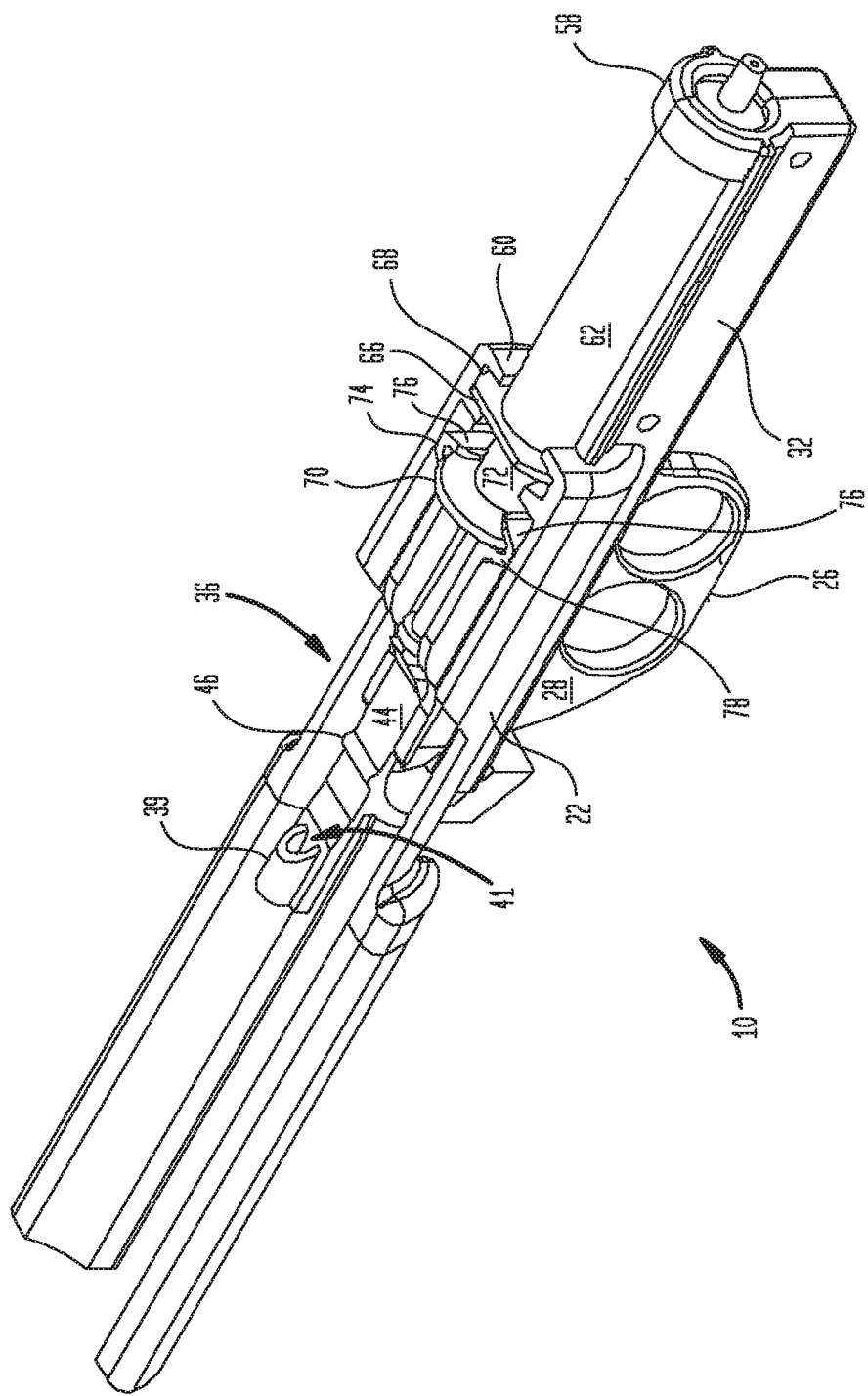
Figure 31:
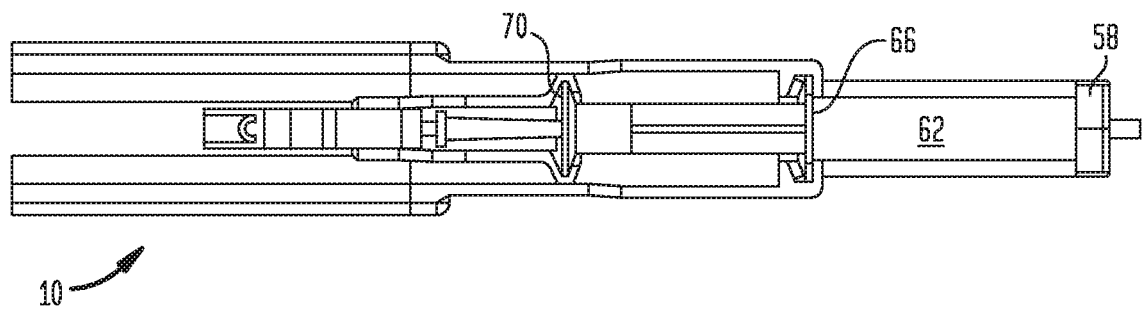
FIGS. 31-37 are respectively a plan view, a right side elevation, a rear elevation, a front elevation, a bottom view, a sectional view along line 36-36 in FIG. 32, and a left side elevation of the alternative embodiment of FIGS. 29 and 30.
Figure 32:
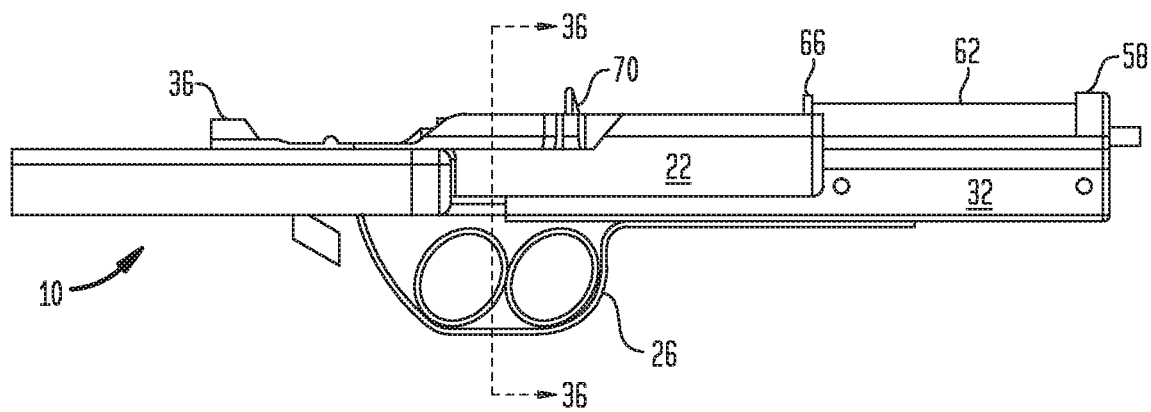
Figure 33:
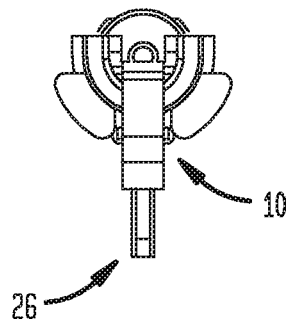
Figure 34:
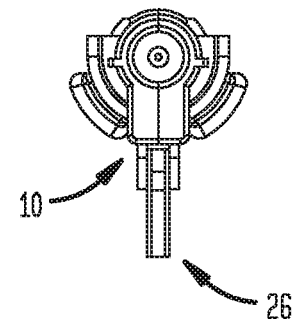
Figure 35:
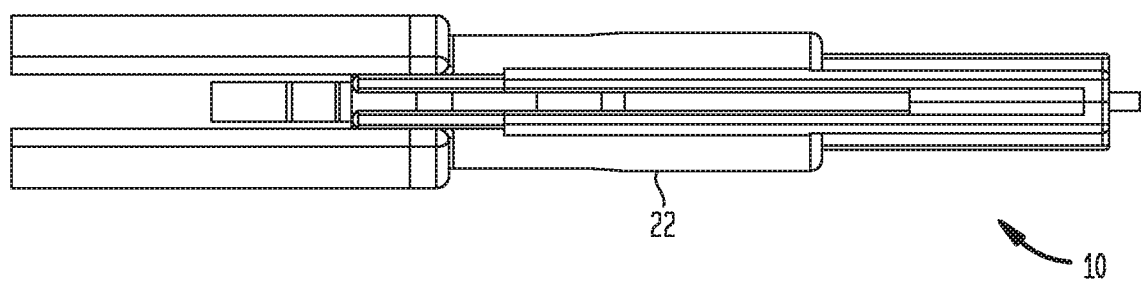

In FIG. 29, the handle of the previous embodiment is largely dispensed with leaving only trigger 26 directly connected to actuator 28 deployed directly under body 22 such that, when a digit of one hand extends through trigger 26, the ball of the thumb of that hand easily falls on medial ridge 46 over which guidewire 12 is passed allowing the clinician to advance the guidewire 12 while retaining good tactile feel for the resistance being encountered. It should be observed that in the embodiment of FIGS. 29 and 30, flanges 66 and 70 are well secured in slots 68 and 74 respectively, while barrel 62 of syringe 54 is secured by forward ring 58, thereby providing positive location of syringe 54. It should be noted that in the embodiment of FIGS. 29-30, the hand engages the fixture much like a hand would grasp the hilt of a sword.

Figure 36:
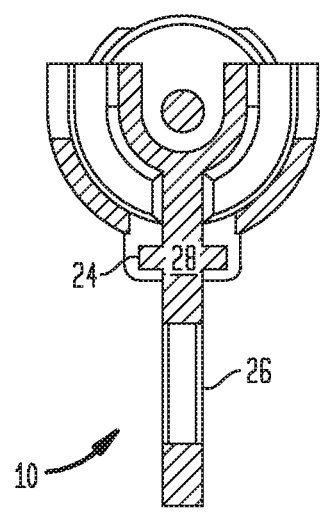
Figure 37:
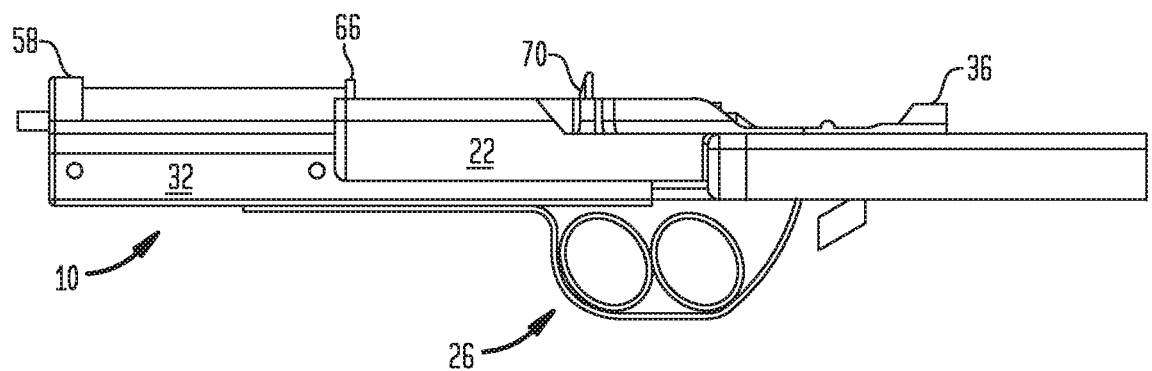
Figure 38:
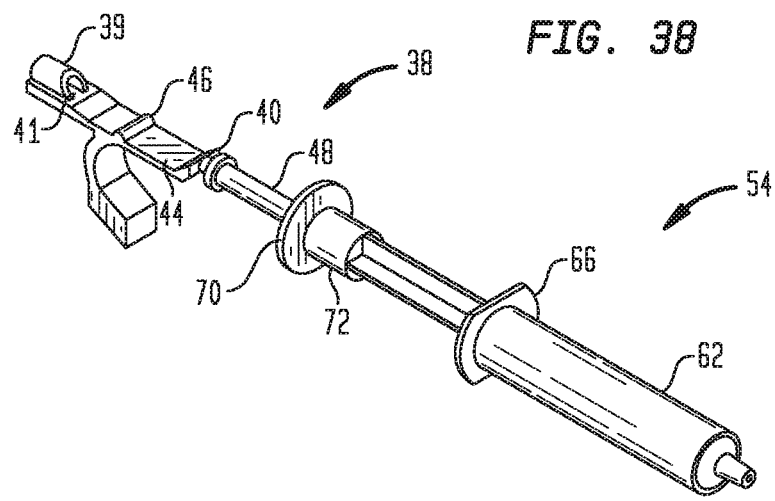
FIGS. 38-40 are exploded views of the embodiment illustrated in FIG. 30.
Figure 39:
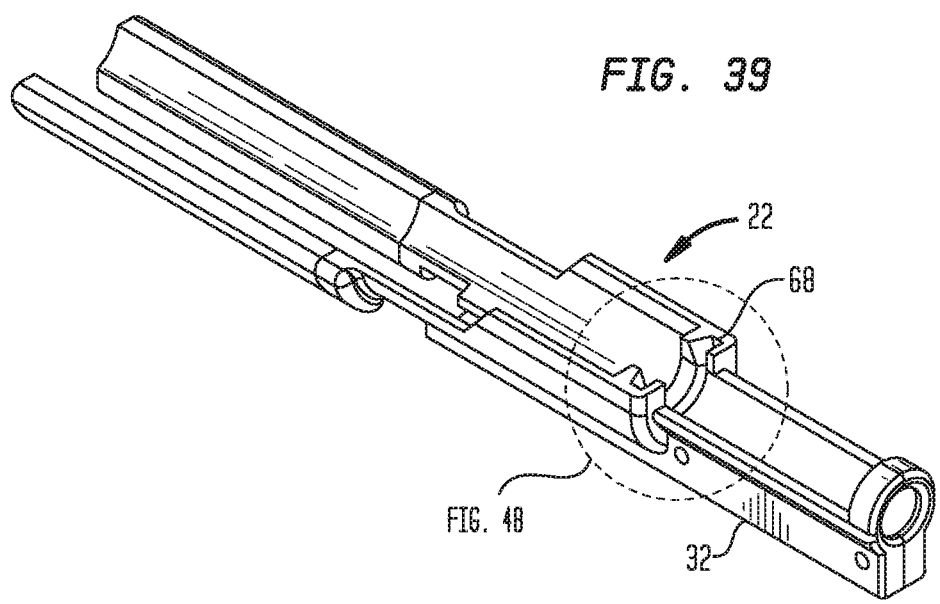
Figure 40:
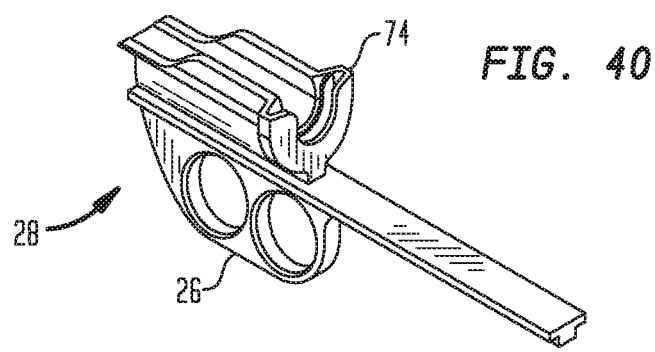
Figure 41:
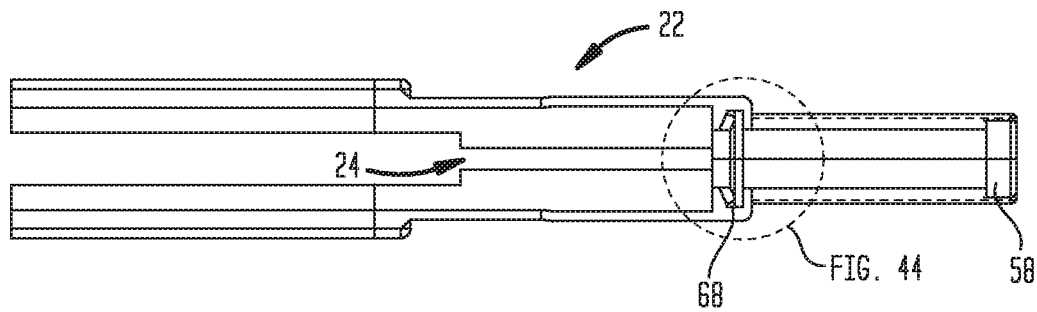
FIGS. 41-55 are detail views illustrating securement of the barrel, plunger and guidewire attachments for the embodiment of FIGS. 29 and 30, in particular

FIGS. 31-37 illustrate details of the internal construction of the fixture of the present invention, note particularly "T"-shaped longitudinal channel 24 (See also FIG. 42) formed in body 22 as shown in FIG. 36 so that actuator 28, having mating "T" shaped portion 25 as shown in FIG. 40, may be advanced and retracted therealong. In FIGS. 38 and 39, the fixture has been disassembled illustrating how the constituent parts are assembled.

Figure 42:
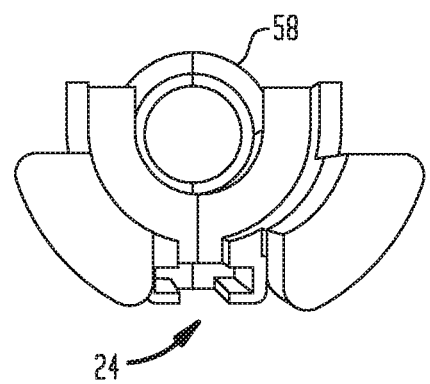
Figure 43:
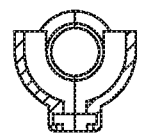
Figure 44:
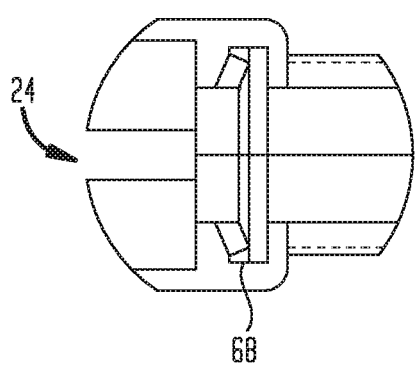
Figure 44A:
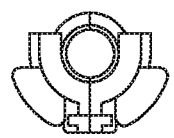
Figure 45:
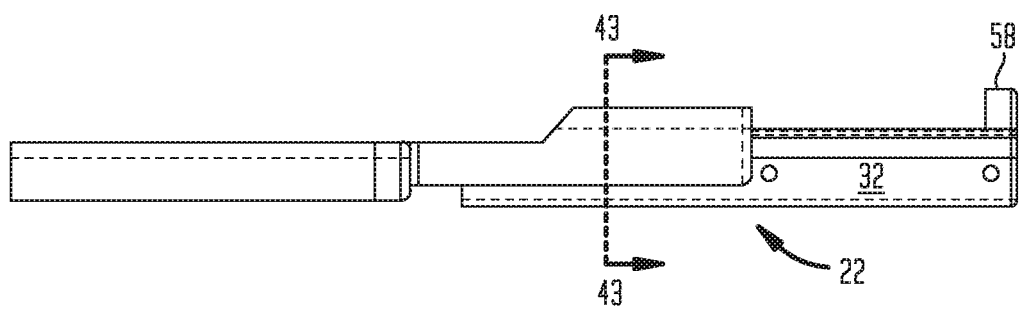
Figure 46:
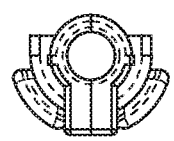
Figure 47:
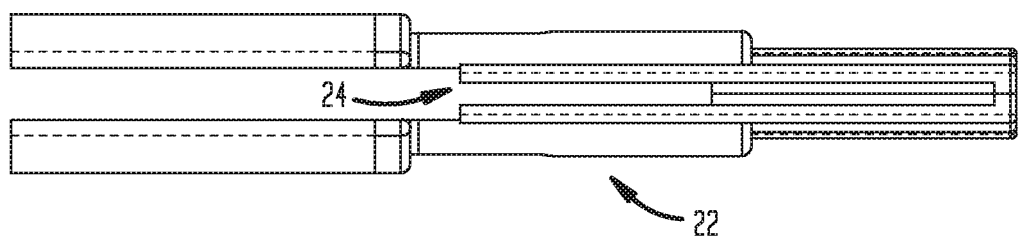
Figure 48:
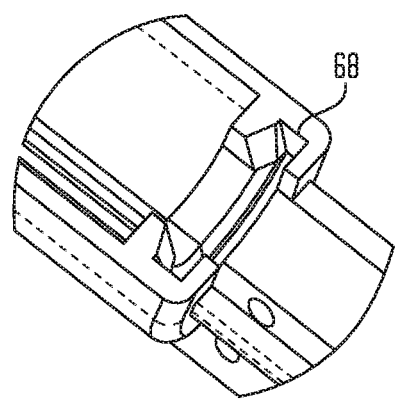
Figure 49:
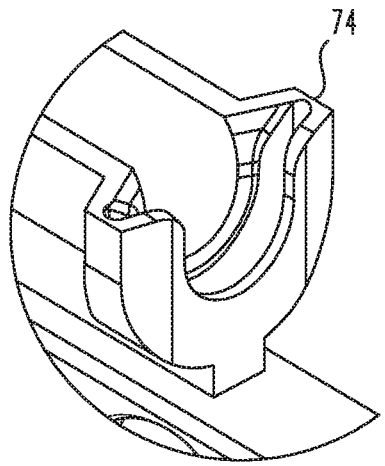
Figure 50:
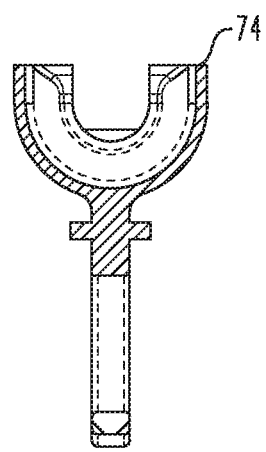
Figure 51:
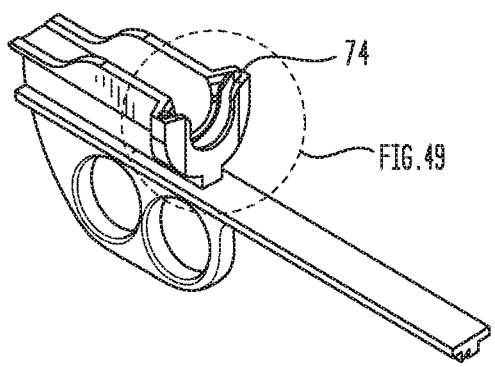
Figure 52:
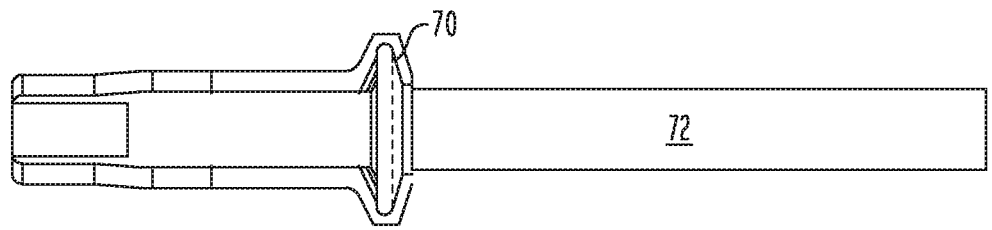
Figure 53:
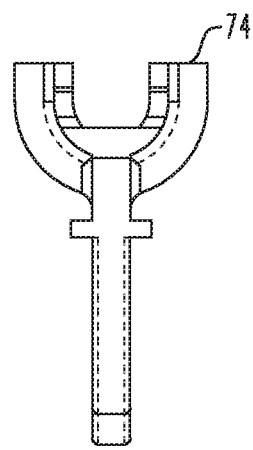
Figure 55:
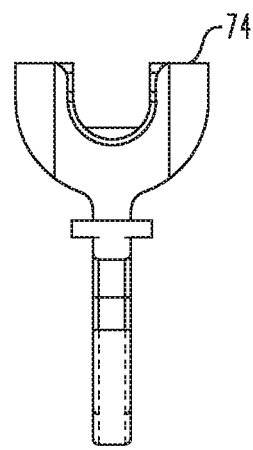
Figure 54:
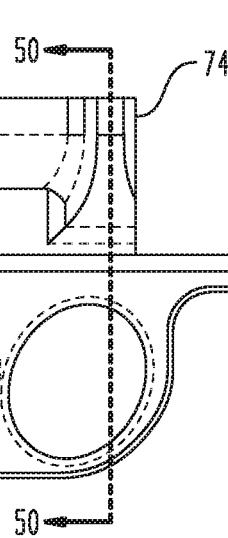

FIGS. 41-48 illustrate other details of the constituent parts. Note longitudinally extending guideway 24 formed in body 22 to restrain movement of slider/actuator 28 thereupon. Note also undercut slot 68 in body 22 engages finger flange 66 for positive positioning thereof. In FIGS. 49-55, details of retention slot 74 having undercut groove 77 for marrying plunger flange 70 to actuator 28 are illustrated. Note again that retention slot 74 encompasses slightly more than 180° of plunger flange 70 thereby enabling positive positioning between the two by virtue of the elasticity of plunger flange 70 and, to a lesser extent, slider actuator 28. Note also the longitudinal undercut as illustrated in FIG. 54. As shown in FIGS. 42, 44, 48, the undercut of groove 77 accommodates the conventional cupping of plunger flange 70 further fixing the relative position thereof.

Figure 56:
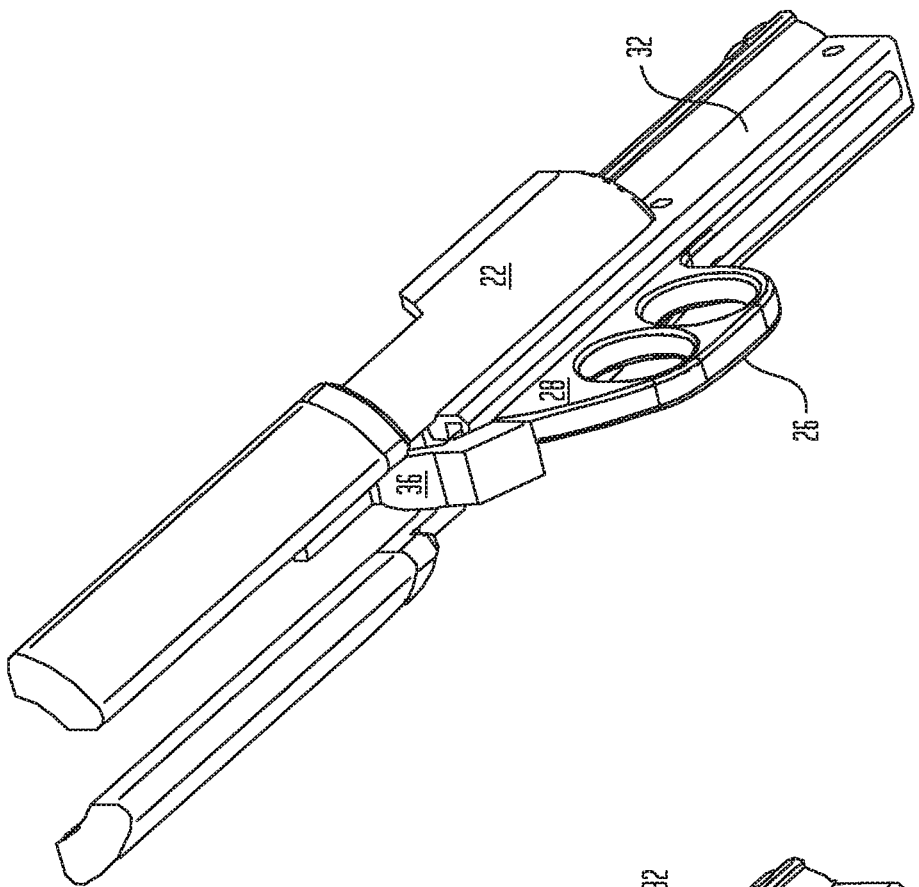
FIGS. 56 and 57 illustrate how suction can be supplied to the syringe barrel by drawing finger rings rearwardly as shown in FIG. 56 and how the plunger of the syringe can be advanced by moving finger rings forwardly as in FIG. 57, which should normally only be done with the syringe out of the body as when the clinician feels that a new start is desirable.
Figure 57:
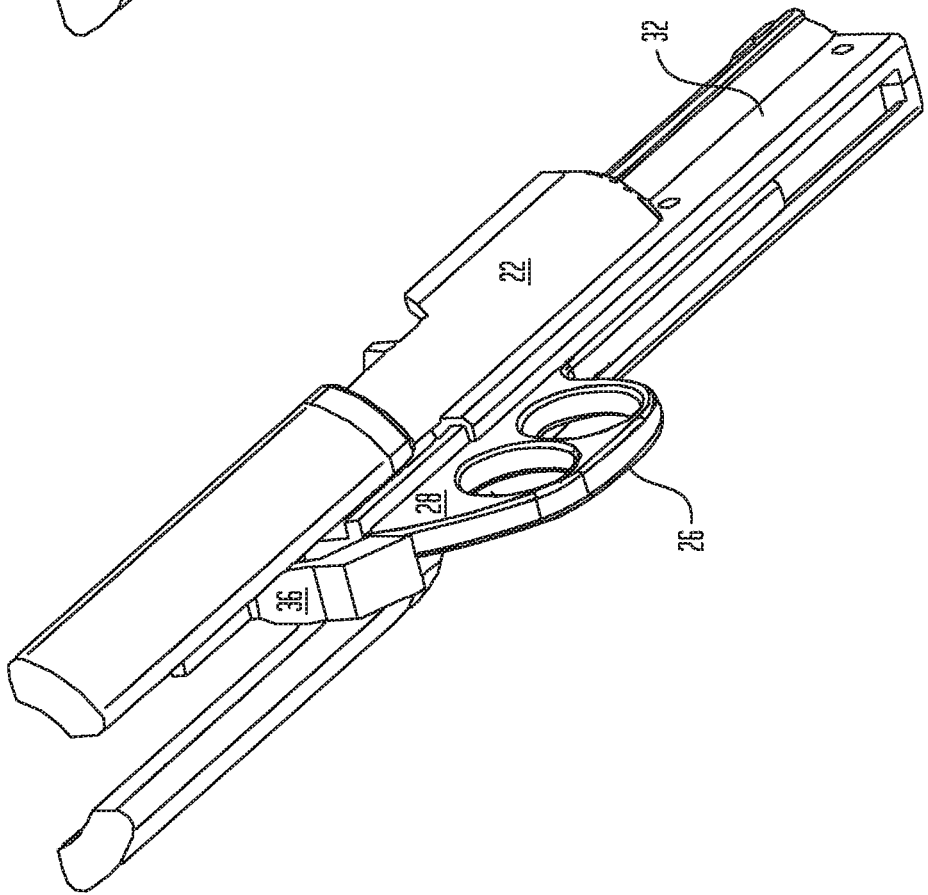

FIGS. 56 and 57 are lower perspectives illustrating motion of slider/actuator 28 along longitudinally extending guideway 24 in body 22 with FIG. 56 illustrating actuator 28 as rearwardly positioned to induce partial vacuum in syringe 54.

Figure 58:
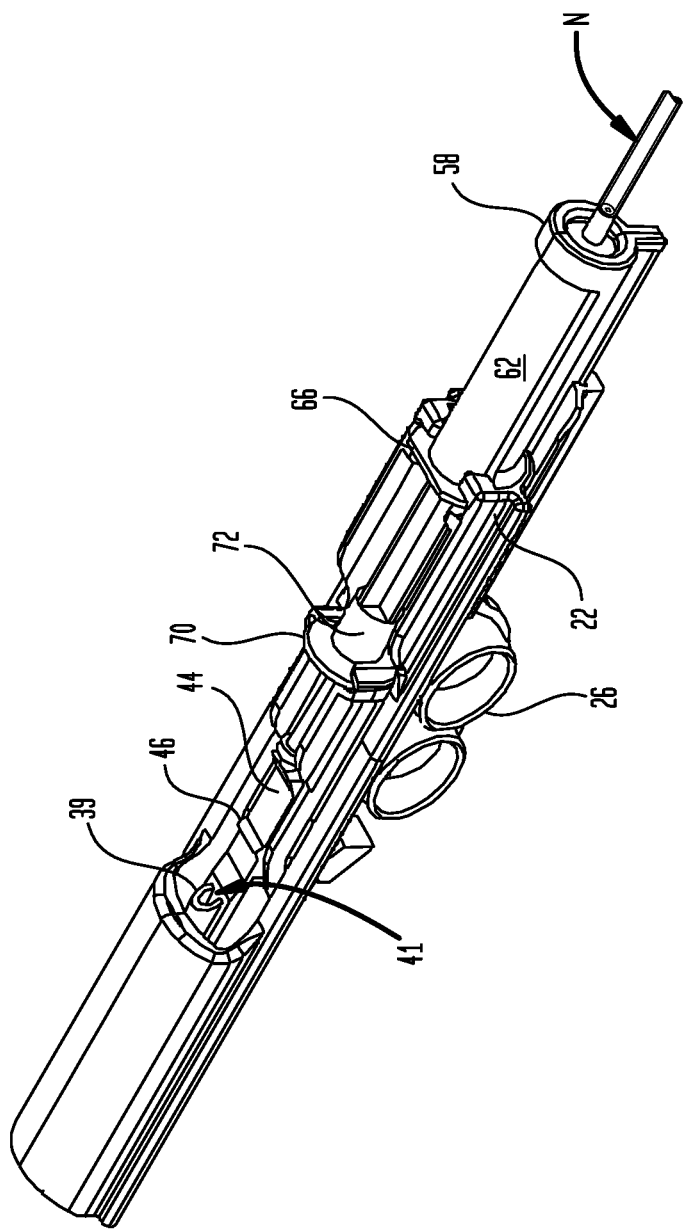
FIG. 58 illustrates an embodiment of the invention having a "hilt handle" configuration.
Figure 59:
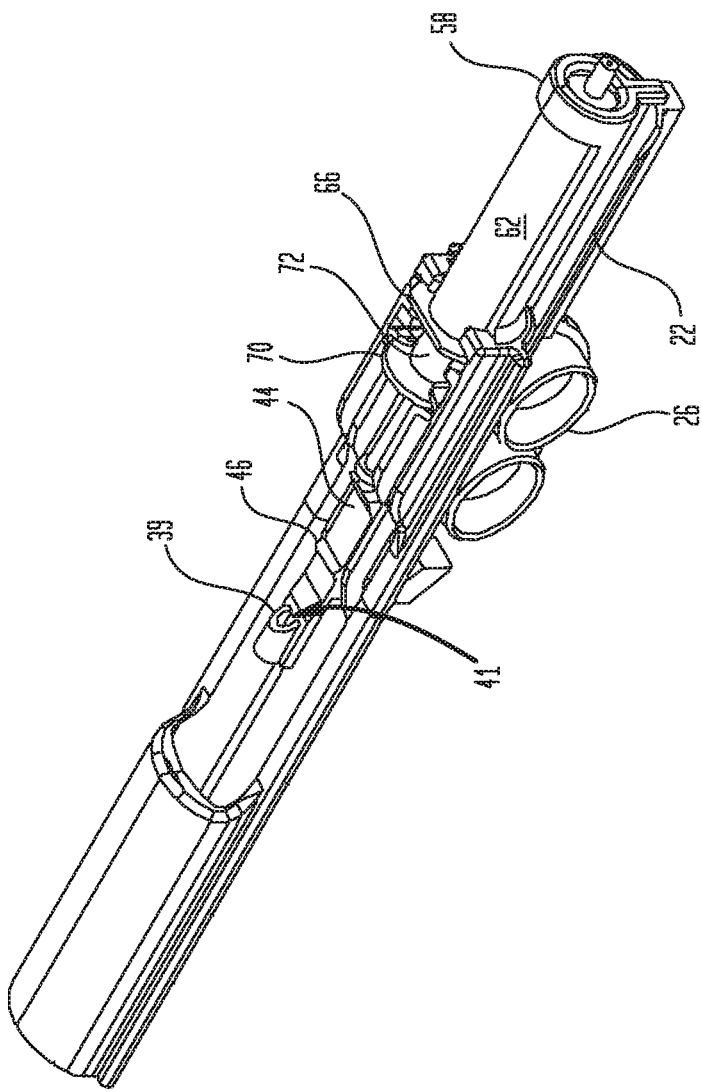
FIG. 59 illustrates the hilt handle embodiment of the invention of FIG. 58 with the slider advanced as would be usual at the beginning of a Seldinger Procedure, while in FIG. 58, the slider has been retracted to induce a slight vacuum in the syringe allowing the practitioner to determine when the needle has entered a fluid filled region, while in making it possible to use the other hand to manipulate an ultrasound for confirmation that the needle is properly positioned.
Figure 60:
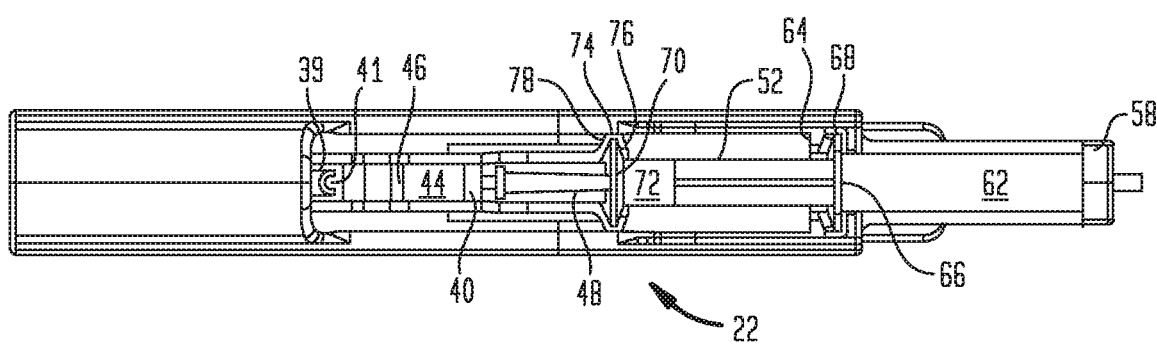
FIGS. 60-66 are respectively a plan view, front elevation, a sectional view taken along 62-62 in FIG. 61, a left side elevation, a right side elevation, a rear elevation, bottom view of the embodiments of FIGS. 58 and 59.
Figure 61:
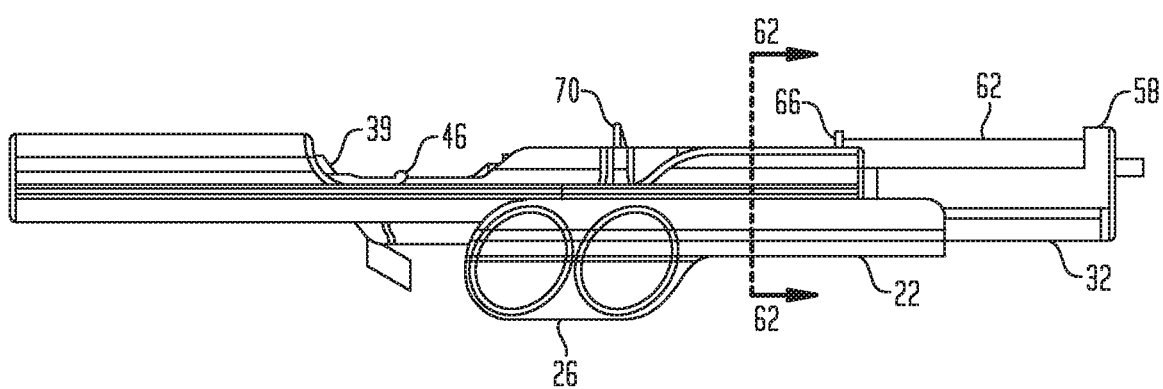

FIGS. 58 and 59 illustrate still another embodiment of the present invention in which shield/hood 97 positively prevents improper insertion of generally annular guidewire cassette 14 (not shown) when generally annular guidewire cassette 14 enters through tunnel 95.

Figure 62:
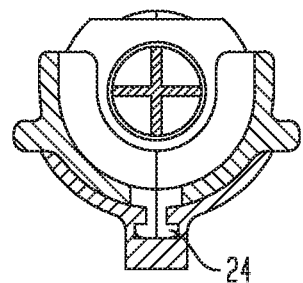
Figure 63:
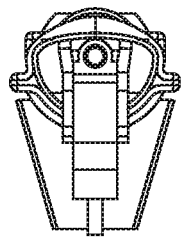
Figure 64:
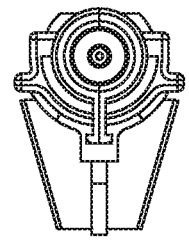
Figure 65:
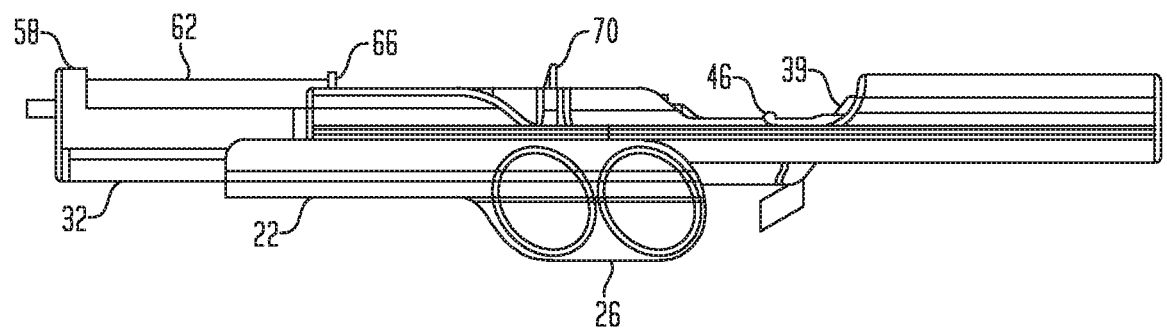
Figure 66:
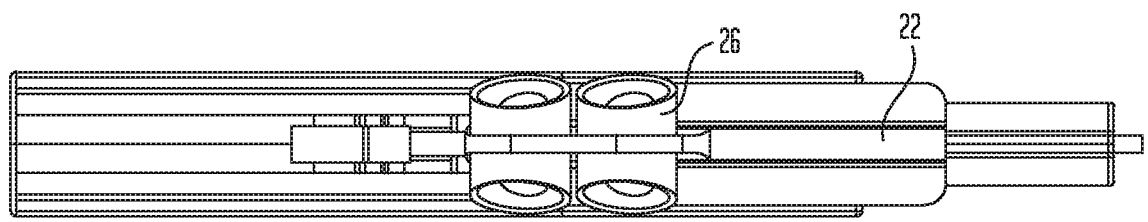

In FIGS. 60-66, details of the internal construction of the fixture are illustrated. Note that longitudinally extending guideway 24 is now incorporated into slider/actuator 28 as shown in FIG. 62.

Figure 67:
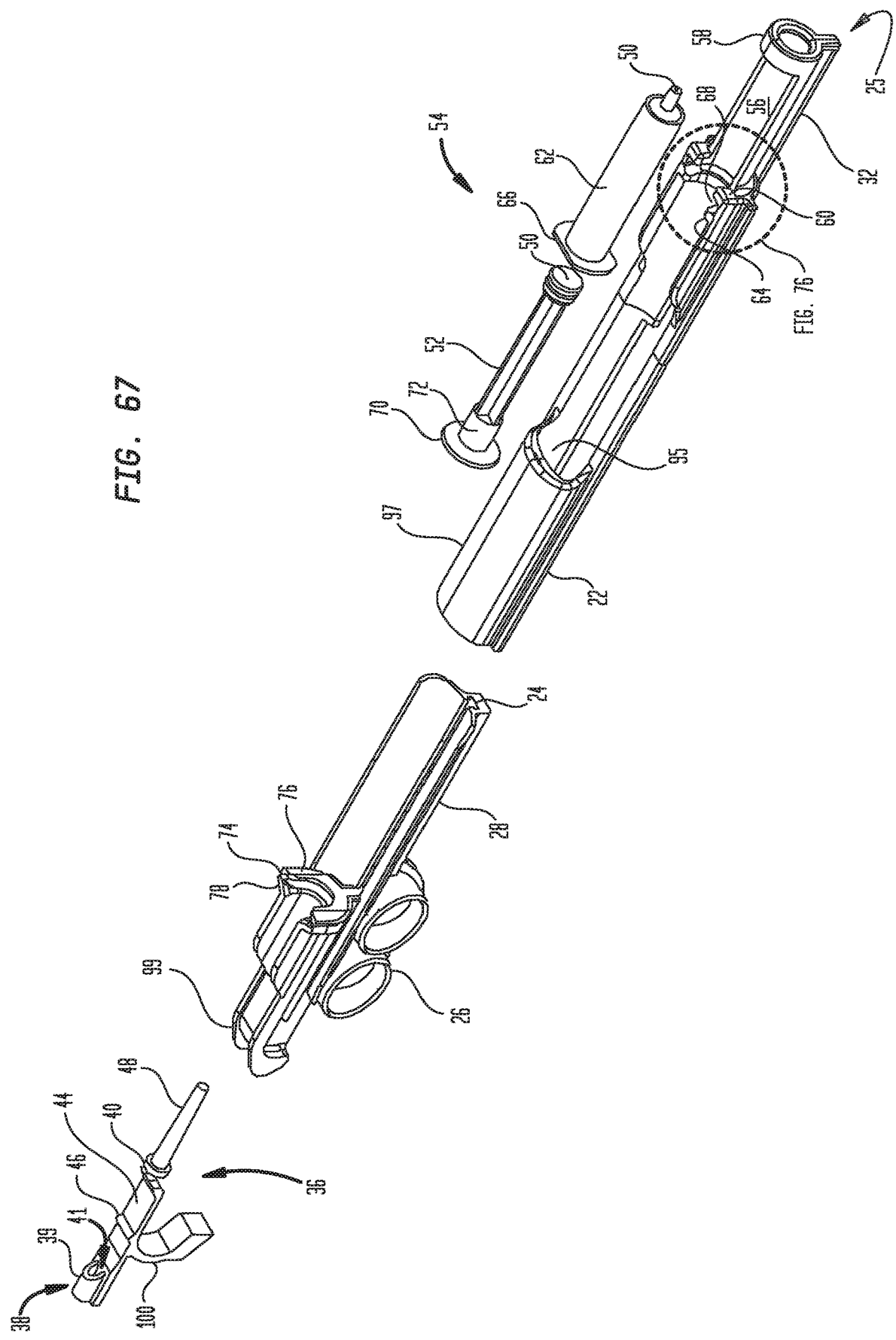
FIG. 67 is an exploded view of the embodiment of FIGS. 58 and 59.
Figure 68:
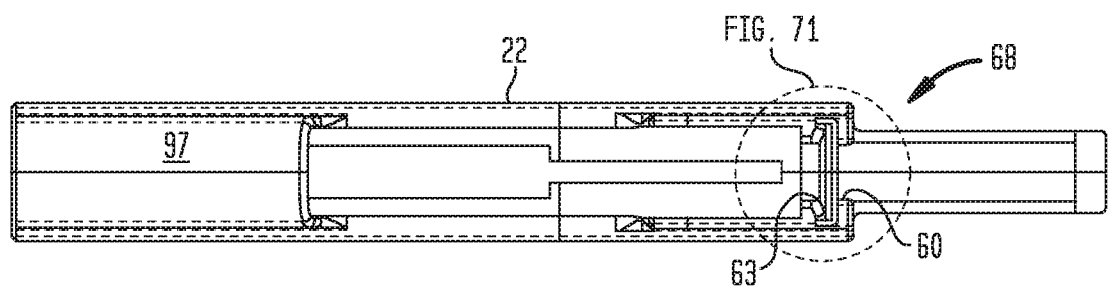
FIGS. 68-76 are detail views illustrating mounting features for ensuring reliable, hold fast, snap-into-position placement of the flange on the barrel of the syringe, in particular
Figure 69:
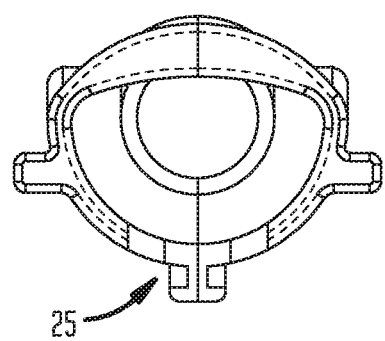
Figure 70:
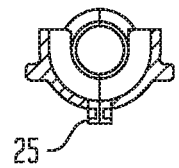
Figure 71:
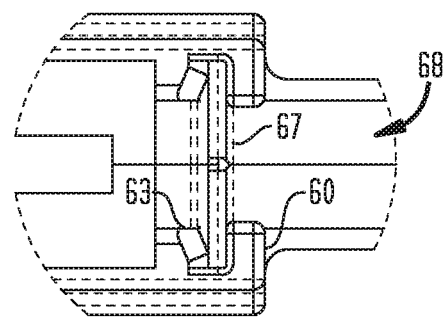
Figure 72:
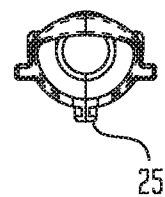
Figure 73:
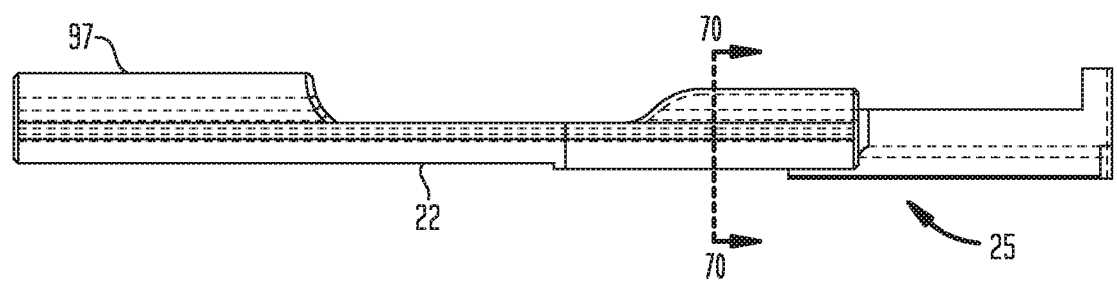
Figure 74:
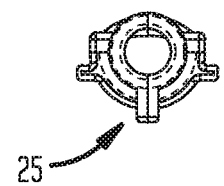
Figure 75:
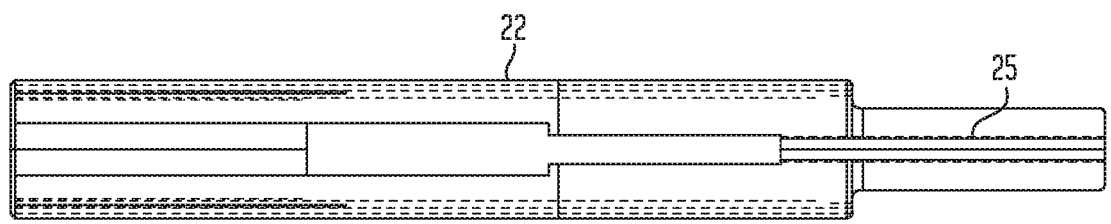
Figure 76:
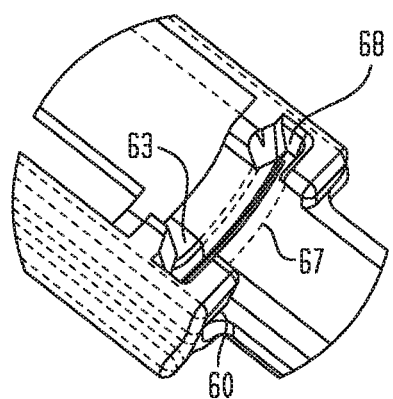
Figure 80:
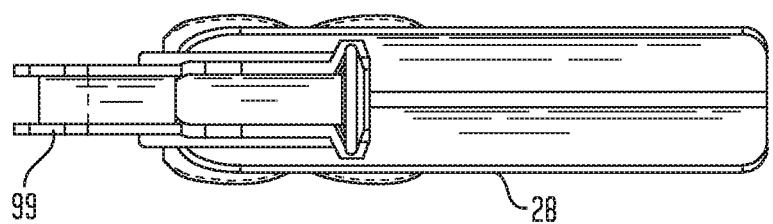
Figure 81:
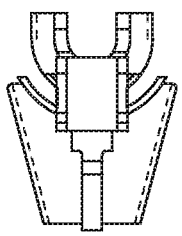
Figure 82:
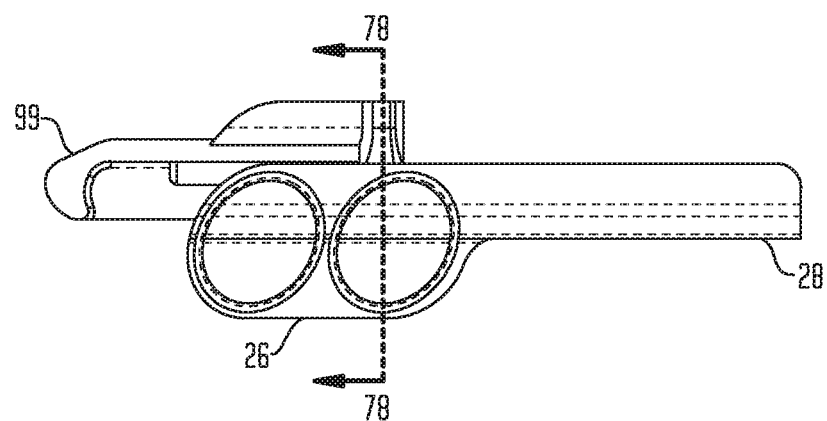
Figure 83:
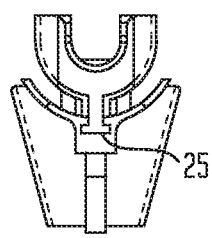

In FIG. 67, note that ramp 99 interlockingly mates with pylon 100 of wire guide feed module 36 for more positive positioning thereof back to slider/actuator 28.

In FIGS. 68-76, details of construction of body 22 are illustrated. Particularly note that in FIG. 71, finger flange slot 68 is longitudinally undercut with undercut groove 67 accepting finger flange 66 to positively position finger flange 66 in body 22 while flexible wall 63 serves to more positively lock finger flange 66 into position in finger flange slot 68. Note also that T-Bar 25 is formed in body 22 in this embodiment while slot 24 is formed in slider/actuator 28.

In FIGS. 77-83, details of the construction of slider/actuator 28 are illustrated. Note particularly that groove 77 engages more than 180° of plunger flange 70 in interference fit to more positively position plunger flange 70 respect to slider/actuator 28.

Figure 84:
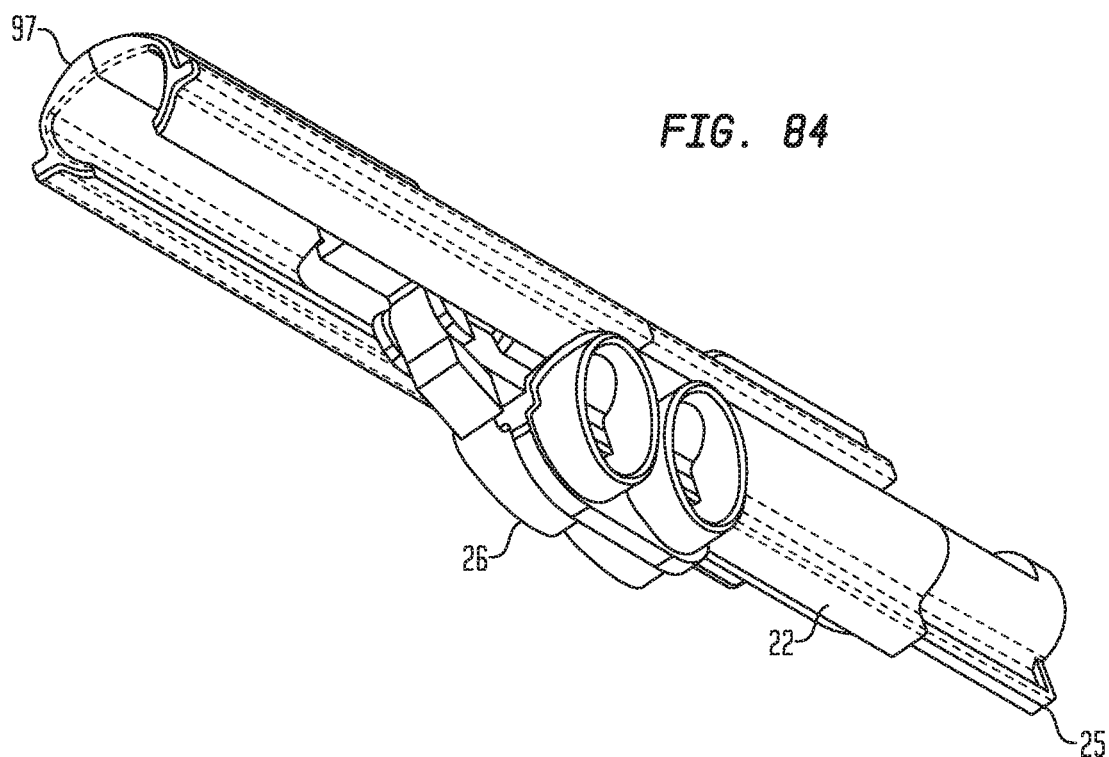
FIGS. 84-85 are lower perspective views illustrating the fixture of the present invention with the slider in the rearward and frontal positions respectively.
Figure 85:
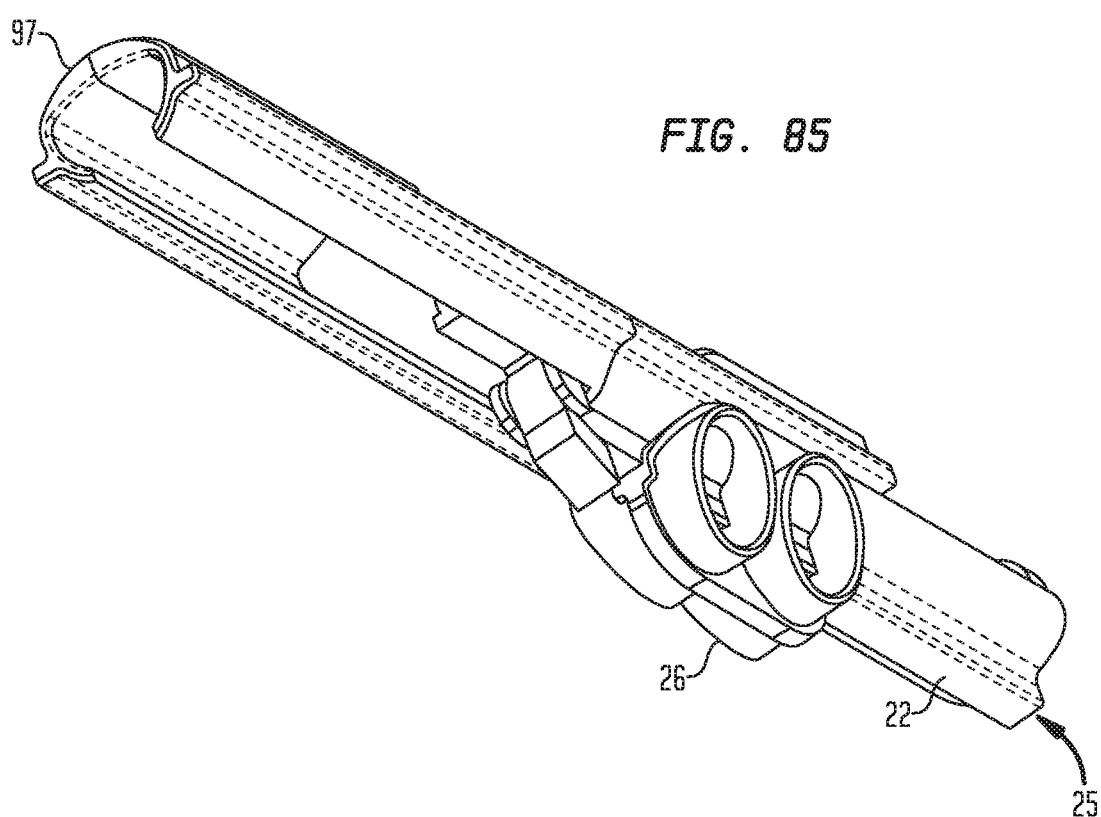

In FIGS. 84-85, a lower perspective illustrates slider/actuator 28 in a rearward position (FIG. 84) as well as a forward position (FIG. 85).

Figure 86A:
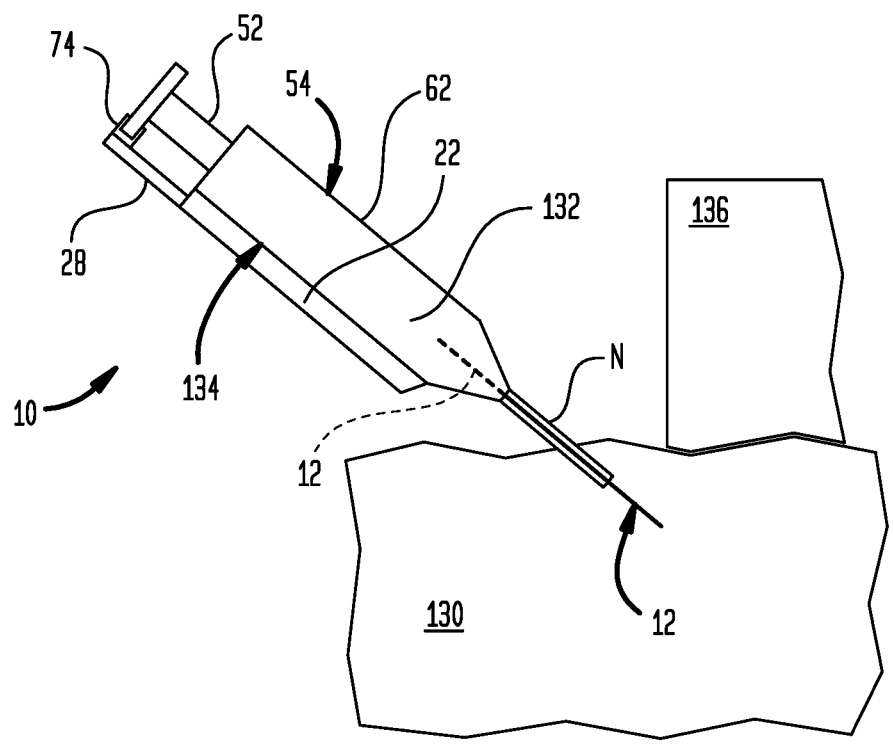
FIGS. 86(a) and 86(b) schematically illustrate a process for inserting a guidewire into an organism and thereafter passing a central line into the organism over the guidewire.

There is illustrated in FIGS. 86(a) and (b) a method of inserting a guidewire 12 into the body of an organism 130, comprising the steps of: providing a fixture 10, operable with one gloved hand having digits, to: (a) advance a hollow bare needle indicated at N of syringe 54 having a plunger 52 into organism 130; (b) manipulate trigger 26 to move the plunger of said syringe to induce partial vacuum therein; and (c) advance guidewire 12 mounted on said fixture into said organism by direct tactile contact between at least one digit of said gloved hand and said guidewire; detecting when said hollow bare needle on said syringe is entering into proper positioning by observation of entry of a fluid 132, whether liquid, gaseous or mixture, into said syringe; stabilizing said guidewire in position within said organism without using said gloved hand operating said fixture; and withdrawing said fixture. Said fixture having: a body 22 with a trap 134 capable of retaining a barrel 62 of the syringe, an actuator 28 movable with respect to said body, said actuator having a trap 74 for the plunger of the syringe as well as a mount for receiving a feed adapter having a feed surface for the guidewire as described herein.

During this process, the inventive device makes it possible for another hand of the operator of said fixture is used to manipulate a probe or transducer 136 of a device for visualization of a location of said guidewire within organism 130.

Figure 86B:
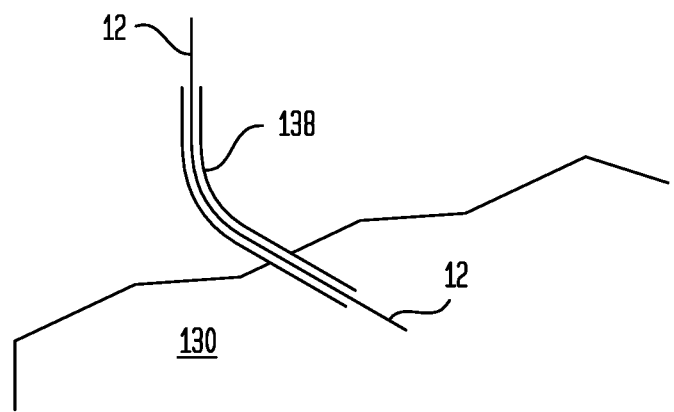

Once the guidewire is inserted, a central line 138 may be placed over said guidewire and passed into said organism after said fixture has been withdrawn, as is shown in FIG. 86(b).

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference, further description is deemed unnecessary. In addition, it should be understood that aspects of the invention and portions of various embodiments may be combined or interchanged either in whole or in part. Furthermore, those of ordinary skill in the art will appreciate that the foregoing description is by way of example only, and is not intended to limit the invention.

As our invention, we claim:

1. In an apparatus for insertion of a guidewire of the class including a generally annular cassette, having an exit opening, the guidewire being inserted through a syringe into a body of a patient:
wherein said syringe is of the type having a barrel with a finger flange, a plunger having a plunger flange and a guidewire passage therethrough and a hollow needle generally co-linear with said guidewire passage through said plunger, and
wherein said generally annular cassette has attached thereto:
a guidewire feed having a receiver configured and dimensioned to couple with said generally annular cassette and a guide fitting comprising a forward tube configured and dimensioned to couple with said plunger and direct said guidewire into said guidewire passage through said plunger of said syringe, said guidewire feed having a wire feed surface between said generally annular cassette and said forward tube;
the improvement comprising:
an insertion device comprising:
a body of said device,
a grip operably connected to said body of said device;
a barreltrap mounted on said body of said device adapted to receive and retain the barrel of said syringe;
an actuator carriage slidably coupled to said body of said device via a guideway, said actuator carriage having attached thereto:
a trigger,
a plunger flange trap adapted to grasp the plunger flange of said plunger of said syringe,
wherein said guideway is formed in either said body of said device or said actuator carriage,
wherein said grip, said trigger and said wire feed surface are disposed such that when the grip is engaged by digits of one hand, a digit of said one hand is able to advance and retract the guidewire through said syringe by engaging the guidewire between said digit of said one hand and the wire feed surface, sensing a degree of resistance encountered by a tip of said guidewire, with another digit of said one hand being able to urge the trigger of said actuator carriage rearwardly and/or forwardly, drawing said plunger rearwardly and/or forwardly while said digits of said one hand continue to engage said grip.

2. The device for insertion of a guidewire of claim 1, wherein said receiver, configured and dimensioned to couple with said generally annular cassette, is spaced rearwardly from said wire feed surface and holds the exit opening of said generally annular cassette generally in line with said wire feed surface, said guide fitting and said guidewire passage through said plunger of said syringe.

3. The device for insertion of a guidewire of claim 2, wherein said guideway is formed in said body of said device.

4. The device for insertion of a guidewire of claim 2, wherein said guideway is formed in said actuator carriage of said device.

5. A method of inserting a hollow needle followed by inserting a guidewire into the body of the patient through said hollow needle comprising utilizing the insertion device according to claim 1.

6. A device for one-handed insertion of a guidewire, comprising:
a body having:
a grip formed in said body,
a mount formed in said body for a syringe of the type having: a plunger; a plunger flange and a guidewire passage through said plunger and a hollow needle co-linear with said guidewire passage through said plunger,
wherein said mount is adapted to receive and retain a barrel of the syringe;
an actuator carriage slidably coupled to said body via a guideway, wherein said guideway is formed in either said body or said actuator carriage,
said actuator carriage having attached thereto:
a trigger,
a flange trap adapted to grasp the plunger flange of the syringe,
a wire guide feed mount adapted to support a generally annular cassette mounted on said actuator carriage and having mounted thereupon:
a guide fitting adapted to couple with said plunger flange and direct said guidewire into said guidewire passage through the plunger of said syringe; and
a wire feed surface between said generally annular cassette and said guide fitting,
a receiver configured and dimensioned to couple with said generally annular cassette,
wherein said grip, said trigger and said wire feed surface are disposed such that when the grip is engaged by the digits of one hand, a digit of said one hand is able to advance the guidewire through said syringe by engaging the guidewire between the digit of said one hand and the wire feed surface, sensing a degree of resistance encountered by a tip of said guidewire, with another digit of said one hand being able to urge the trigger of said actuator carriage rearwardly and/or forwardly, drawing said plunger rearwardly and/or forwardly while said digits of said one hand continue to engage said grip.

7. The device for insertion of a guidewire of claim 6, wherein said receiver configured and dimensioned to couple with said generally annular cassette is spaced rearwardly from said flange trap and holds an exit of said generally annular cassette generally in line with said wire feed surface, said guide fitting and said guidewire passage through plunger of said syringe.

8. The device for insertion of a guidewire of claim 7, wherein said guideway is formed in said body of said device.

9. The device for insertion of a guidewire of claim 7, wherein said guideway is formed in said actuator carriage of said device.

10. A method of inserting a hollow needle followed by inserting a guidewire into a body of a patient through said hollow needle comprising utilizing the device for one-handed insertion of a guidewire according to claim 6.

11. A method of inserting a guidewire into a body of an organism, comprising the steps of:
providing a fixture, operable by an operator with one gloved hand having digits, to:
(a) advance a hollow needle of a syringe having a plunger into said organism;
(b) manipulate the plunger of said syringe to induce partial vacuum therein; and
(c) advance a guidewire mounted on said fixture into said organism by direct tactile contact between at least one digit of said gloved hand and said guidewire;
detecting when said hollow needle on said syringe is entering into proper positioning by observation of entry of a fluid, whether liquid, gaseous or mixture, into said syringe;
stabilizing said guidewire in position within said organism without using said gloved hand operating said fixture; and
withdrawing said fixture;
said fixture having:
a body with a trap capable of retaining a barrel of the syringe,
an actuator movable with respect to said body of said fixture, said actuator having a trap for the plunger of the syringe as well as a mount for receiving a feed adapter having a feed surface for the guidewire, said feed adapter being adapted to couple to a cassette having the guidewire therein.

12. The method of inserting a guidewire into the body of the organism of claim 11, wherein another hand of the operator of said fixture is used to manipulate a probe or transducer of a device for visualization of a location of said guidewire within said organism.

13. The method of inserting a guidewire into the body of the organism of claim 11, comprising the further step of: thereafter placing a tubular line over said guidewire and passing said tubular line into said organism after said fixture has been withdrawn.

14. A device for one-handed insertion of a hollow needle and a guidewire, comprising:
a body having:
a grip formed in said body or attached thereto,
a mount formed in said body for a syringe of the type having: a plunger; a plunger flange and a guidewire passage through said plunger and the hollow needle co-linear with said guidewire passage through said plunger,
wherein said mount is adapted to receive and retain a barrel of the syringe;
an actuator carriage slidably coupled to said body via a guideway, wherein said guideway is formed in either said body or said actuator carriage,
said actuator carriage having:
a trigger,
a flange trap adapted to grasp the plunger flange of the syringe,
a wire feed surface,
wherein said grip, said trigger and said wire feed surface are disposed such that when the grip is engaged by digits of one hand, a digit of said one hand is able to advance the guidewire through said syringe by engaging the guidewire between the digit of said one hand and the wire feed surface, sensing a degree of resistance encountered by a tip of said guidewire, with another digit of said one hand being able to urge the trigger of said actuator carriage rearwardly and/or forwardly, drawing said plunger rearwardly and/or forwardly while said digits of said one hand continue to engage said grip.

15. A method of inserting a hollow needle followed by inserting a guidewire into a body of a patient through said hollow needle comprising utilizing the device for one-handed insertion of a hollow needle and guidewire according to claim 14.

\* \* \* \* \*